United States Patent

Driver et al.

[11] Patent Number: 5,066,646
[45] Date of Patent: Nov. 19, 1991

[54] AMPHOTERICIN DERIVATIVES

[75] Inventors: Michael J. Driver; Alexander R. Greenlees; David T. MacPherson, all of Epsom, England

[73] Assignee: Beecham Group p.l.c., Brentford, England

[21] Appl. No.: 448,698

[22] Filed: Dec. 11, 1989

[30] Foreign Application Priority Data

Dec. 19, 1988 [GB] United Kingdom ............... 8829592

[51] Int. Cl.$^5$ ..................... A61K 31/70; C07H 17/08
[52] U.S. Cl. ....................................... 514/31; 536/6.5
[58] Field of Search ............... 536/6.5; 514/31; 549/267, 269

[56] References Cited

U.S. PATENT DOCUMENTS 4,041,232 8/1977 Sipos et al. ................... 536/6.5

Primary Examiner—Elli Peselev
Attorney, Agent, or Firm—Hopgood, Calimafde, Kalil, Blaustein & Judlowe

[57] ABSTRACT compounds of formula (I) or pharmaceutically acceptable salts thereof;

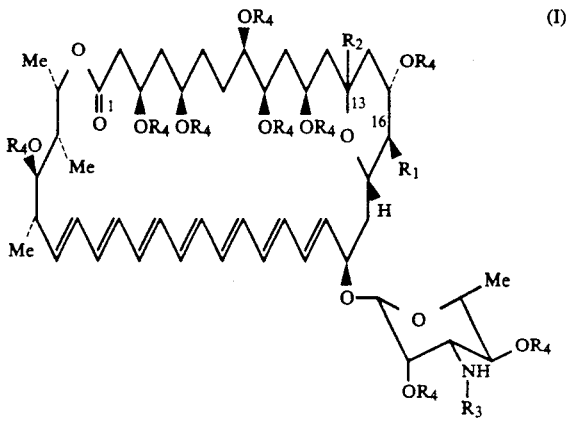

wherein $R_1$ is a gorup -X-Y where X is a carbonyl group and Y is hydrogen, $C_{1-8}$ alkyl, $C_{2-8}$ alkenyl, or optionally substituted aryl or heteroaryl; $R_2$ is hydroxy or $C_{1-8}$ alkoxy; $R_3$ is hydrogen or an amine protection group; and each $R_4$ is hydrogen; their preparation, compositions containing them and their use as antifungal agents are described.

7 Claims, No Drawings

AMPHOTERICIN DERIVATIVES

The present invention relates to novel compounds, their preparation and their use in the treatment of fungal infections in animals, including humans.

The polyene macrolide amphotericin B, produced by *Streptomyces nodosus*, is widely used for the treatment of fungal infections.

Amphotericin B is the only complex polyene macrolide whose molecular structure and absolute configuration have been firmly established by x-ray crystallographic analysis. Amphotericin B has the formula (A):

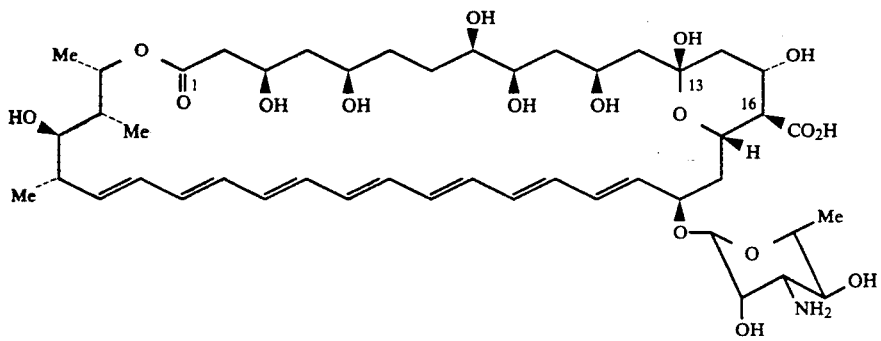
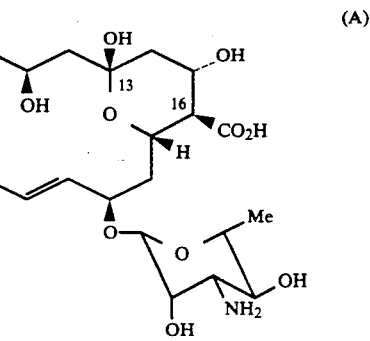

Derivatives of amphotericin B having a 16-position lower alkyl ester group and acid addition salts formed with the primary amine group of the sugar moiety have been prepared in attempts to satisfy the need for a less toxic antifungal agent than amphotericin B. Derivatives of this type are for example described in European Patent Publication No. 0 010 297 (Schering) and U.S. Pat. No. 4,235,993 (Squibb).

Novel derivatives of amphotericin B have now been prepared in which the 16-position carboxyl group is replaced by a functional group in a lower oxidation state, which derivatives have been shown to have antifungal activity and have potential utility as anti-fungal agents.

Accordingly, the present invention provides a compound of formula (I) or a pharmaceutically acceptable salt thereof:

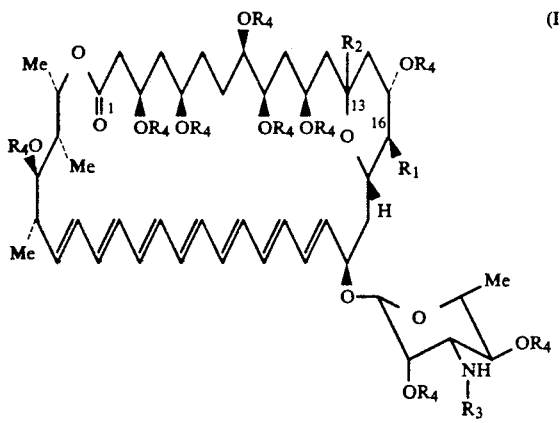

wherein $R_1$ is a group -X-Y where X is a carbonyl group and Y is hydrogen, $C_{1-8}$ alkyl, $C_{2-8}$ alkenyl, or optionally substituted aryl or heteroaryl; $R_2$ is hydroxy or $C_{1-8}$ alkoxy; $R_3$ is hydrogen or an amine protection group; and each $R_4$ is hydrogen.

Unless otherwise specified, an alkyl or alkenyl group preferably has from 1 to 6 carbon atoms, more preferably 1 to 4 carbon atoms and may be straight-chain or branched.

When used herein, the term aryl includes carbocyclic groups such as phenyl and naphthyl, preferably phenyl. The term heteroaryl includes 5- or 6- membered monocyclic and 9- or 10- membered bicyclic heteroaryl.

In addition, 5- or 6- membered monocyclic and 9- or 10- membered bicyclic heteroaryl preferably contain one or two heteroatoms selected from nitrogen, oxygen and sulphur which in the case of there being more than one heteroatom may be the same or different. When 9- or 10- membered bicyclic heteroaryl, the two rings are fused, preferably with one 5- or 6- membered ring containing a single heteroatom.

Optional substituents for aryl and heteroaryl groups may be selected from OH, $C_{1-6}$ alkyl, $C_{1-6}$ alkoxy, L-halogen, and amino optionally substituted by $C_{1-6}$ alkyl.

Values for $R_1$ include $C_{1-6}$ alkanoyl such as formyl and acetyl, $C_{2-6}$ alkenoyl such as pent-4-enoyl, aroyl such as benzoyl, and heteroaroyl such as 2-pyrrolylcarbonyl.

Values for $R_2$ include hydroxy and methoxy, preferably hydroxy.

Values for $R_3$ include hydrogen, acetyl, trifluoroacetyl, 9-fluorenylmethoxycarbonyl, trichloroethoxycarbonyl, 2-methylsulphonylethoxycarbonyl and 2-trimethylsilylethoxycarbonyl. Preferably $R^3$ is hydrogen, acetyl, trifluoroacetyl or 9-fluorenylmethoxycarbonyl. More preferably $R_3$ is hydrogen Also included within the scope of compounds in which $R_3$ is an amine protection group are further amino group derivatives, in particular acyl derivatives bearing a basic substituent such as N-D-lysyl and N-D-ornithyl derivatives, guanidine derivatives, and N-glycosyl derivatives. The preparation of further amino group derivatives is described in European Patent Publication No. 0 010 297 (Schering), European Patent Publication No. 0 031 722 (Dumex) and U.S. Pat. No. 4,195,172.

The term pharmaceutically acceptable salt encompasses solvates and hydrates. Thus where compounds of formula (I) or pharmaceutically acceptable salts thereof form solvates or hydrates, these also form an aspect of the invention.

The compounds of formula (I) wherein $R_3$ is hydrogen can form acid addition salts with acids, such as conventional pharmaceutically acceptable acids, for example hydrochloric, hydrobromic, phosphoric, acetic, fumaric, salicylic, citric, lactic, mandelic, tartaric, oxalic, methanesulphonic, aspartic and ascorbic. The invention also extends to quaternary salts.

The present invention also provides a process for the preparation of compounds of formula (I) which process comprises the reaction of a compound of formula (II):

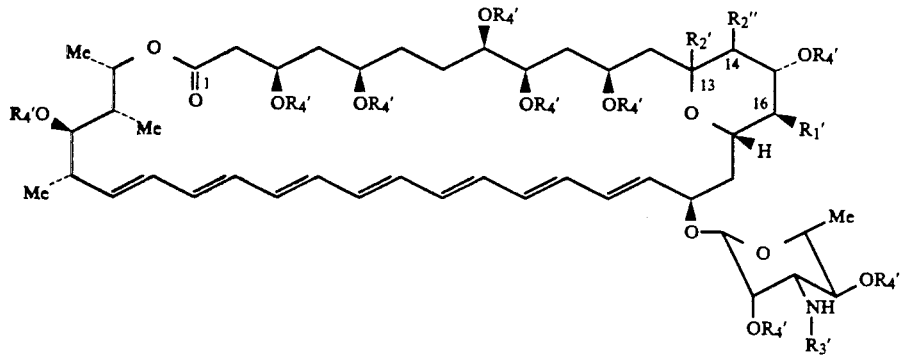

wherein $R_1'$ is an activated carboxylic acid derivative; $R_2'$ is $C_{1-8}$ alkoxy and $R_2''$ is hydrogen, or $R_2'$ and $R_2''$ together are a bond; $R_3'$ is an amine protection group; and each $R_4'$ is a silyl protecting group, with:

(a) an organometallic reagent Y-M where Y is $C_{1-8}$ alkyl, $C_{2-8}$ alkenyl or optionally substituted aryl or heteroaryl and M is a metallic residue, to give a compound of formula (III):

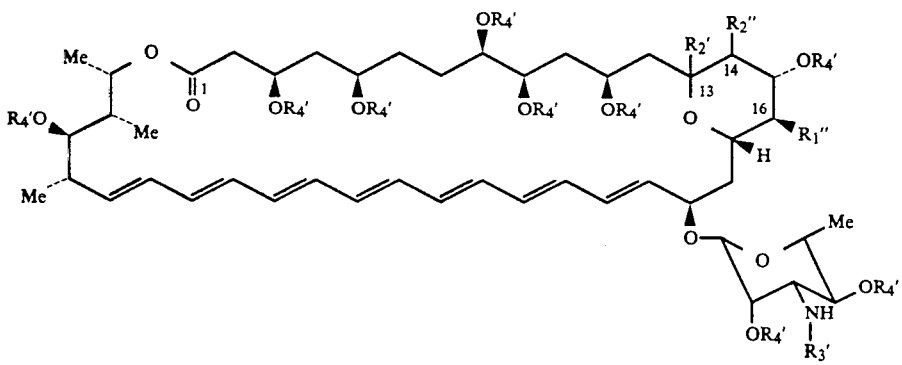

wherein $R_1''$ is a group -X-Y where X is a carbonyl group, and Y is $C_{1-8}$ alkyl, $C_{2-8}$ alkenyl, or optionally substituted aryl or heteroaryl; and $R_2'$, $R_2''$, $R_3'$ and $R_4'$ are as defined for formula (II); or (b) a reducing agent, to give a compound of formula (III) wherein $R_1''$ is -CH$_2$OH; and $R_2'$, $R_2''$, $R_3'$ and $R_4'$ are as defined for formula (II), followed by oxidation of the $R_1''$ -CH$_2$OH group to give a compound of formula (III) wherein $R_1''$ is -CHO; and $R_2'$, $R_2''$, $R_3'$ and $R_4'$ are as defined for formula (II); and thereafter, optionally or as necessary and in any appropriate order converting $R_1''$ to $R_1$, converting $R_2'$ to $R_2$ when $R_2''$ is hydrogen or converting $R_2'$ to $R_2$ and $R_2''$ to hydrogen when $R_2'$ and $R_2''$ together are a bond, converting $R_3'$ to $R_3$, removing the $R_4'$ silyl protecting groups, interconverting $R_2$, interconverting $R_3$, and forming a pharmaceutically acceptable salt.

It will be understood that the term activated carboxylic acid derivative when used herein in relation of process variant (a) or (b) includes a carboxylic acid group modified by chemical reaction into an activated form amenable to the tranformation specified in that particular process variant.

The term activated carboxylic acid derivative includes alkyl, aryl and heteroaryl esters and thioesters, acid halides and acid anhydrides, and amides such as N-methyl-N-methoxy amides.

An $R_1'$ carboxylic acid derivative activated for reaction with an organometallic reagent or a reducing agent is suitably a thioester and preferably a heteroarylthioester such as a pyridylthioester.

Favourably $R_1'$ is a 2-pyridylthioester.

The reaction with an organometallic reagent or a reducing agent may be carried out using a compound of formula (II) in which $R_2'$ is $C_{1-8}$ alkoxy, preferably methoxy or ethoxy and $R_2''$ is hydrogen, or using a compound of formula (II) in which $R_2'$ and $R_2''$ together are a bond, or mixtures thereof. Favourably a compound of formula (II) is used in which $R_2'$ and $R_2''$ together are a bond.

$R_3'$ amine protection groups are chosen such that they do not react adversely with the organometallic reagent, reducing agent or oxidising agent. Preferably, an $R_3'$ amine protection group is readily removable subsequent to the transformations specified under process variants (a) and (b) to provide a compound of formula (I) in which $R_3$ is hydrogen.

Values for $R_3'$ include acetyl, trifluoracetyl, 9-fluorenylmethoxycarbonyl, trichloroethoxycarbonyl, 2-methylsulphonylethoxycarbonyl and 2-trimethylsilylethoxycarbonyl.

In process variant (a), $R_3'$ is suitably acetyl or trifluoroacetyl, preferably trifluoroacetyl.

In process variant (b), $R_3'$ is suitably acetyl or 9-fluorenylmethoxycarbonyl, preferably 9-fluorenylmethoxycarbonyl.

Suitable $R_4'$ silyl protecting groups include trimethylsilyl, triethylsilyl and t-butyldimethylsilyl.

Preferably $R_4'$ is triethylsilyl.

Organometallic reagents (Y-M) for reaction with compounds of formula (II) according to process variant (a) include reagents in which the metallic element of the metallic residue (M) may be magnesium, lithium, copper, zinc, manganese or cadmium.

Preferably the organometallic reagent is an organomagnesium halide or Grignard Reagent such as an organomagnesium bromide or iodide, for example methylmagnesium bromide, phenylmagnesium bromide or pyrrolylmagnesium bromide.

The reaction with the organometallic reagent may be carried out under conditions generally used for such reactions, for example using anhydrous reagents under an inert atmosphere and at reduced temperature.

The compound of formula (II) is preferably reacted with an excess of a Grignard Reagent, for example from 2 to 30 molar equivalents and preferably from 5 to 15 molar equivalents, in an inert solvent such as tetrahydrofuran or diethylether. The reaction is generally carried out at reduced temperature in the range $-78°$ C. to room temperature and preferably in the range $-20°$ C. to room temperature. Reaction times may vary between 0.1 and 6 hours but a reaction time between 0.1 and 1 hour is generally sufficient.

Where the Grignard Reagent is an alkenylmagnesium halide and is present in molar excess, it will be understood that the double bond may undergo an addition reaction with further Grignard Reagent to give a chain-extended alkenyl moiety.

A suitable reducing agent for reaction with compounds of formula (II) according to process variant (b) is lithium borohydride. The reaction may be carried out in an inert solvent such as diethyl ether or tetrahydrofuran, preferably diethyl ether.

The oxidation of the resulting $R_1''$ -CH$_2$OH group may be carried out using modified Swern oxidising conditions such as a mixture of trifluoroacetic anhydride, dimethyl sulphoxide, triethylamine and 1,1,3,3-tetramethylurea in dichloromethane.

In compounds of formula (III) where $R_2'$ is $C_{1-8}$ alkoxy and $R_2''$ is hydrogen, $R_2'$ may be converted to an $R_2$ hydroxy under acid-catalysed conditions after removal of the $R_4'$ silyl protecting groups, using water or a mixture of water and tetrahydrofuran as solvent, preferably using a solvent mixture comprising 10-50% water in tetrahydrofuran.

Similarly, compounds of formula (III) where $R_2'$ and $R_2''$ together are a bond may be hydrated under acid-catalysed conditions to give compounds of formula (I) in which $R_2$ is hydroxy.

A suitable acid catalyst for these reactions is 10-camphorsulphonic acid or pyridinium p-toluene sulphonate.

Compounds of formula (III) in which $R_2'$ and $R_2''$ together form a bond may be converted directly to compounds of formula (I) in which $R_2$ is $C_{1-8}$ alkoxy by the acid-catalysed addition of the appropriate $C_{1-8}$ alkyl alcohol, or alternatively, indirectly via initial hydration of the double bond, followed by exchange of the $R_2$ hydroxyl group, so formed, using the appropriate $C_{1-8}$ alkyl alcohol. These conversions are carried out under anhydrous conditions, suitably in the presence of 10-camphorsulphonic acid, or pyridinium p-toluenesulphonate.

Where $R_3$ in compounds of formula (I) is hydrogen, conversion of a readily removable $R_3'$ amine protection group to $R_3$ hydrogen may be carried out under basic conditions.

An $R_3'$ amine protection group such as trifluoroacetyl may be removed using a base such as ammonia or potassium carbonate in anhydrous methanol.

An $R_3'$ amine protection group, such as 9-fluorenylmethoxycarbonyl, may be removed under basic conditions in a solvent such as methanolic dimethyl sulphoxide. Suitable bases for amine deprotection include ammonia, dialkylamines such as dimethylamine and diethylamine, trialkylamines such as triethylamine, cyclic amines and especially cyclic secondary amines such as morpholine, piperazine and more especially piperidine, and diazabicyclic bases such as 1,5-diazabicyclo[4.3.0]-non-5-ene (DBN) and preferably 1,8-diazabicyclo[5.4.0]undec-7-ene (DBU).

The amine deprotection may be carried out using from 1-10 equivalents of base, preferably from 1-2 equivalents, at reduced or elevated temperatures, for example from $-30°$ C. to $50°$ C. and preferably from $0°$ C. to room temperature, over a time period ranging from 1 minute to 5 hours and preferably from 30 minutes to 2.5 hours.

$R_4'$ silyl protecting groups in compounds of formula (III) may be removed using known deprotection methods, for example using a solution of hydrogen fluoride-pyridine in tetrahydrofuran, at normal or reduced temperature, for example from $-10°$ C. to $50°$ C. and preferably from $0°$ C. to room temperature, over a time period up to 60 hours and preferably from 4 to 24 hours.

Intermediate compounds of formula (II) may be prepared from the natural product amphotericin B by carrying out the following steps in any appropriate order:
(a) activating the 16-position carboxy group to give an $R_1'$ activated carboxylic acid derivative;
(b) selectively exchanging the 13-position anomeric hydroxyl group to give an $R_2'$ $C_{1-8}$ alkoxy group or preparing a compound in which $R_2'$ and $R_2''$ together are a bond;
(c) protecting the amine function of the 19-position sugar moiety with an $R_3'$ amine protection group.
(d) converting free hydroxyl groups to -OR$_4'$ where $R_4'$ is a silyl protecting group.

The 16-position carboxyl group may be converted to an $R_1'$ 2-pyridylthioester using 2-thiopyridyl chloroformate in an inert solvent such as tetrahydrofuran, diethyl ether or dichloromethane, preferably diethyl ether, at temperatures ranging from reduced to elevated, such as from $-20°$ C. to $50°$ C., preferably $0°$ C. to room temperature.

The 13-position anomeric hydroxyl group may be selectively exchanged using the appropriate $C_{1-8}$ alkyl alcohol in the presence of an acid catalyst such as 10-camphorsulphonic acid or pyridinium p-toluene sulphonate under anhydrous conditions. The reaction may be carried out in an inert solvent such as tetrahydrofuran and the alcohol may act either wholly or partially as the solvent. The reaction is conveniently carried out in the presence of an H$_2$O-scavenger such as molecular sieves and/or under an inert atmosphere.

$R_3'$ amine protection groups may be introduced by standard procedures. For example, an $R_3'$ acetyl or trifluoroacetyl amine protection group may be introduced by reaction of the primary amine with acetic anhydride, or ethyl trifluoroacetate in the presence of base such as diisopropylethylamine, in a methanol-dimethyl sulphoxide or methanoldimethylformamide solvent mixture at reduced to normal temperatures, for example at 0° C.

An $R_3'$ 9-fluorenylmethoxycarbonyl amine protection group may be introduced by addition of 9-fluorenylmethyl chloroformate to a solution of the primary amine in methanol-dimethylformamide under anhydrous conditions, in the presence of a base such as potassium carbonate.

Alternatively an $R_3'$ 9-fluorenylmethoxycarbonyl group may be introduced by addition of N-(9-fluorenyl-methoxycarbonyloxy)succinimide to a slurry of the primary amine in methanoldimethylformamide under anhydrous conditions in the presence of a base such as pyridine.

Free hydroxyl groups may be silylated using standard procedures. The reaction with silyating agents such as trimethylsilyl trifluoromethanesulphonate and triethylsilyl trifluoromethanesulphonate may be carried out in an inert solvent, for example dichloromethane, hexane or diethyl ether, under an inert atmosphere at reduced temperatures, for example from 0° C. to 5° C. The reaction is conveniently effected using an excess of the silylating agent in the presence of a weak base, for example a pyridine derivative such as 2,6-lutidine. Alternatively, when a liquid, the base may replace the solvent. The reaction time is dependent on the size of the silyl group, ranging from a few minutes for a trimethylsilyl group to several hours for larger silyl groups.

The introduction of $R_4'$ silyl protecting groups is accompanied by elimination or partial elimination of the 13-position substituent such that in compounds of formula (II) variables $R_2'$ and $R_2''$ may be $C_{1-8}$ alkoxy and hydrogen respectively or $R_2'$ and $R_2''$ may together be a bond. The extent of the elimination varies according to the solvent; it is significant when the solvent is dichloromethane, but negligible when the solvent is n-hexane or diethyl ether.

Where the silylation reaction results in a mixture of compounds, these may be separated by chromatographic techniques. Alternatively the preparation of compounds of formula (I) may proceed using a mixture of compounds of formula (II).

Certain intermediate compounds of formula (II) and (III) and precursors thereto prepared from amphotericin B are novel compounds and as such form part of the invention.

If required, compounds of formula (I) in which $R_2$ is hydroxy and/or $R_3$ is hydrogen may be converted to compounds of formula (I) in which $R_2$ is $C_{1-8}$ alkoxy and/or $R_3$ is an amine protection group using steps (b) and (c) hereinbefore described for the preparation of intermediate compounds of formula (II)

The compounds of the formula (I) and their pharmaceutically acceptable salts are anti-fungal agents, potentially useful in combating fungal infections in animals, including humans. For example they are potentially useful in treating topical fungal infections in man caused by, among other organisms, species of Candida. Trichochyon, Microsporum or Epidermophyon, or in mucosal infections caused by Candida albicans (e.g. thrush and vaginal candidiasis). They may also be used in the treatment of systemic fungal infections caused by, for example Candida albicans, Cryptococcus neoformans, Asperqillus fumigatus, Coccidioides, Paracoccidioides, Histoplasma or Blastomyces spp. They may also be of use in treating eumycotic mycetoma, chromoblastomycosis, and phycomycosis.

The invention further provides a pharmaceutical composition comprising a compound of the formula (I) or a pharmaceutically acceptable salt thereof together with a pharmaceutically acceptable diluent or carrier. The composition is preferably for human use in tablet, capsule, injectable or cream form.

For human use, the antifungal compounds of the formula (I) or pharmaceutically acceptable salts thereof can be administered alone, but will generally be administered in admixture with a pharmaceutical carrier selected with regard to the intended route of administration and standard pharmaceutical practice. For example, they may be administered orally in the form of a tablet containing such excipients as starch or lactose, or in a capsule or ovule either alone or in admixture with excipients, or in the form of an elixir or suspension containing a flavouring or colouring agent. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral and parenteral administration to human patients, it is expected that the daily dosage level of the antifungal compounds of the formula (I) will be from 0.1 to 1 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

Within the indicated dose range, no adverse toxicological effects have been observed with the compounds of the invention which would preclude their administration to suitable patients for the treatment of fungal infections.

The present invention further provides a compound of formula (I) or a pharmaceutically acceptable salt thereof for use as an active therapeutic substance.

A compound for use as an active therapeutic substance is intended for use in the treatment of disorders in animals including humans. As stated above, compounds of formula (I) and their pharmaceutically acceptable salts have anti-fungal activity and are potentially useful in combating fungal infections in animals including humans.

Accordingly the present invention further provides a compound of formula (I) or a pharmaceutically acceptable salt thereof for use in the treatment of fungal infections.

The present invention additionally provides a method of treatment of fungal infections in animals, including humans, which comprises administering an effective anti-fungal amount of a compound of formula (I) or a pharmaceutically acceptable salt thereof to the animal.

The present invention also provides the use of a compound of formula (I) or a pharmaceutically acceptable salt thereof for the manufacture of a medicament for use as an active therapeutic substance in the treatment of fungal infections in animals, including humans.

The following Examples illustrate the preparation of compounds of the invention and the following Descriptions illustrate the preparation of intermediates thereto.

DESCRIPTION 1

N-Acetyl-13-O-methyl-amphotericin B (D1)

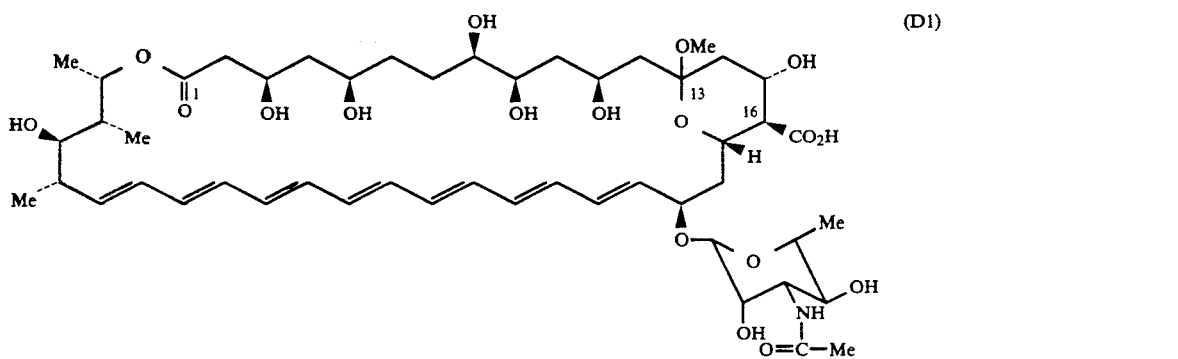

N-Acetyl amphotericin B[1] (0.70 g, 0.71 mmol) and anhydrous d-10-camphorsulphonic acid (0.06 g, 0.25 mmol) were stirred in a mixture of dry methanol (15 ml) and dry tetrahydrofuran (2.5 ml) at room temperature under nitrogen for 0.5 hours. Triethylamine (0.03 g, 0.04 ml, 0.26 mmol) was added, the mixture was concentrated to approximately 3 ml and added to diethylether (400 ml). The precipitate was filtered and washed with ethyl acetate to give the title compound (D1) as a yellow powder.

[1]Nicolaou et al. m J. American Chem Soc., 110, 4660, (1988).

Hplc: Reverse phase ODS 5 μ 250×4.6 mm column; eluant 78% Methanol-22% pH 3 phosphate buffer - 1 ml/min; detection wavelength 350 nm; Retention time: 4.8 minutes.

DESCRIPTION 2

N-Acetyl-13-O-methyl-3,5,8,9,11,15,35,2',4'-nona-O-triethylsilylamphotericin B (2-pyridylthio) ester and N-acetyl-3,5,8,9,11,15,35,2',4'-nona-O-triethylsilyl-13,14-anhydroamphotericin B (2-pyridylthio) ester (D2)

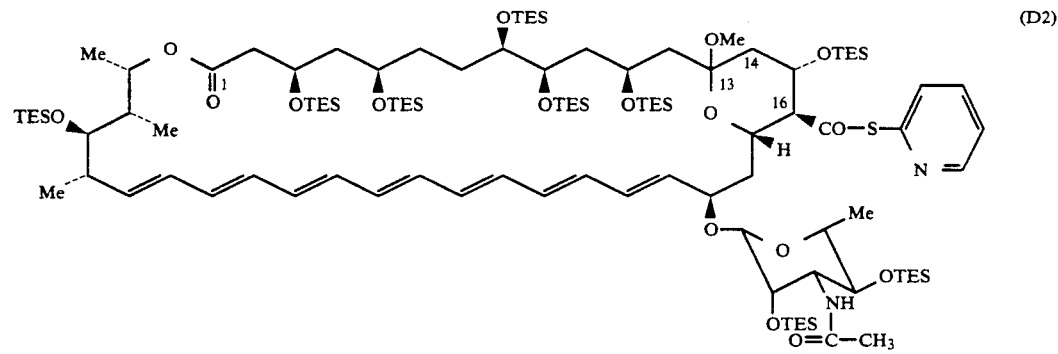

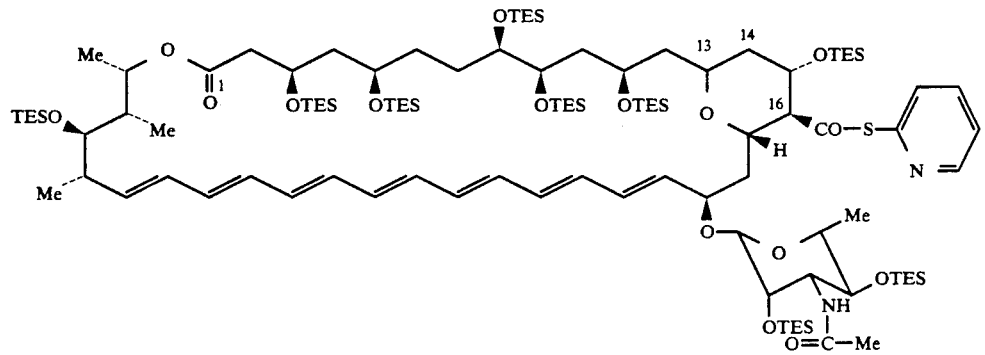

N-Acetyl-13-O-methylamphotericin B (D1) (0.94 g, 0.95 mmol) was suspended in dry dichloromethane (50 ml) at 0° C. under a nitrogen atmosphere and 2,6-lutidine (1.98 g, 2.15 ml, 18.50 mmol) followed by triethylsilyl trifluoromethane sulphonate (3.76 g, 3.22 ml, 14.00 mmol) were added via syringe. After stirring at 0° C. for 40 minutes, the mixture was poured into diethyl ether-/ice cold 0.2 M sodium bisulphate solution. The product was extracted into diethyl ether and the organic extracts were dried over anhydrous magnesium sulphate, filtered and evaporated in vacuo.

The crude product was stirred at 0° C. in dry diethyl ether (15 ml) and treated with triethylamine (106 mg, 0.15 ml, 1.04 mmol) followed by 2-thiopyridyl chloroformate (180 mg, 5.3 ml of 34 mg/ml solution in dichloromethane, 1.04 mmol). After stirring at 0° C. for 30 minutes, the mixture was diluted with diethyl ether (50 ml), dried over anhydrous magnesium sulphate, filtered and evaporated in vacuo. Purification by flash chromatography on silica gel eluting with n-hexane/ethyl acetate mixtures gave a mixture of the title compounds as a yellow foam.

HPLC. Normal phase—Waters radially compressed silica column. Eluant 15% ethyl acetate in n-hexane-2 ml/min. Detection wavelength 406 nm. Retention times : Major product (13-O-methyl derivative) 6.3 minutes. Minor product (13,14-anhydro derivative) 7.0 minutes.

DESCRIPTION 3

N-Acetyl-16-acetyl-16-decarboxy-13-O-methyl-3,5,8,9,11,15,35,2',4'-nona-O-triethylsilylamphotericin B and N-acetyl-16-acetyl-16-decarboxy-3,5,8,9,11,15,35,2',4'-nona-O-triethylsilyl-13,14-anhydroamphotericin B (D3)

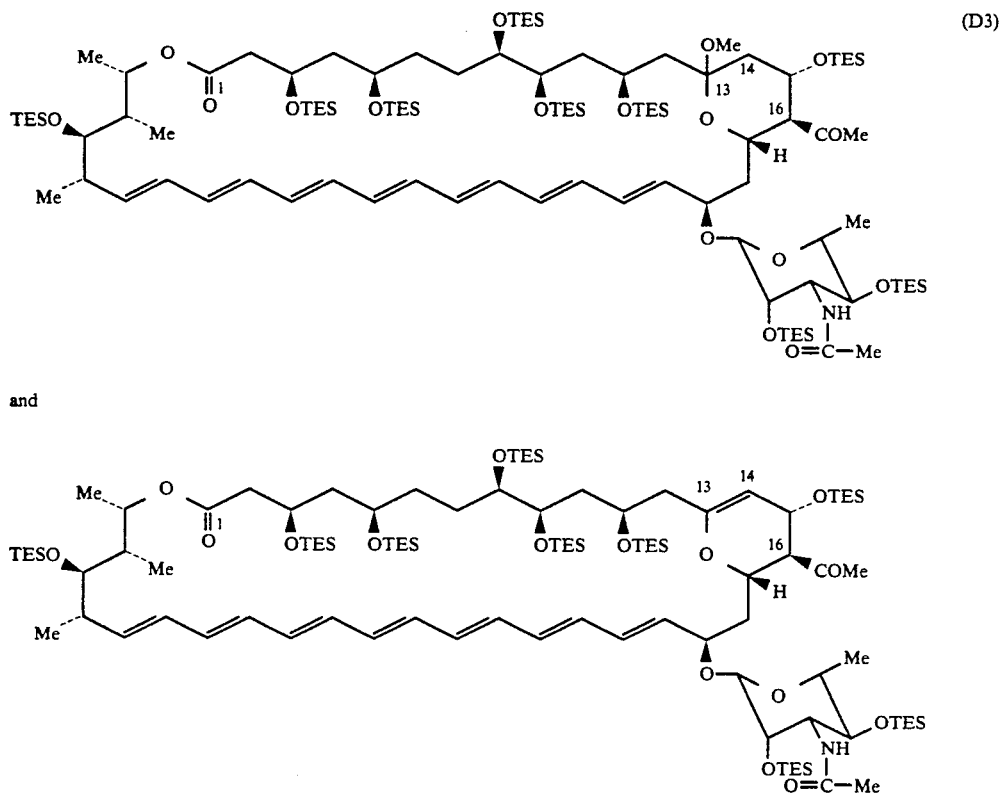

The product mixture of Description 2 was stirred at 0° C. in dry tetrahydrofuran (5 ml) under a nitrogen atmosphere and methyl magnesium bromide (0.37 ml of 3 M solution in diethyl ether, 1.11 mmol) was added via syringe. After 15 minutes at 0° C. a further 0.37 ml of methylmagnesium bromide solution was added and the mixture was stirred for a further 10 minutes at 0° C. The mixture was poured into diethyl ether/water and the product was extracted into diethyl ether. The combined organic extracts were dried over anhydrous magnesium sulphate, filtered and concentrated in vacuo. Purification by flash chromatography on silica gel eluting with 4% diethyl ether in dichloromethane gave a mixture of the title compounds.

HPLC. Normal phase-conditions as in Description 2. Retention times : major product (13-O-methylderivative) 3.0 minutes. Minor product (13,14-anhydro derivative) 3.6 minutes.

DESCRIPTION 4

N-(9-Fluorenylmethoxycarbonyl)amphotericin B (D4)

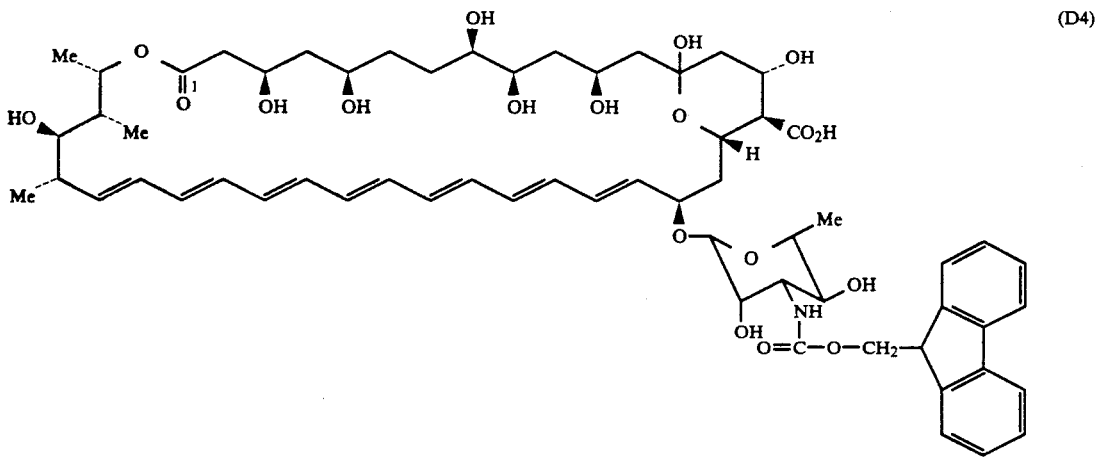

(D4)

To a solution of amphotericin B (0.50 g, 0.54 mmol) and anhydrous potassium carbonate (0.17 g, 1.2 mmol) in dry dimethylsulphoxide (10 ml) and dry methanol (2ml) under a nitrogen atmosphere at 0 C., was added solid 9-fluorenylmethyl chloroformate (0.21 g, 0.81 mmol). After stirring for 1 hour a further portion of 9-fluorenylmethyl chloroformate (0.04 g, 0.17 mmol) was added. After 0.25 hours the reaction mixture was poured into distilled water (200 ml). The precipitate was collected by centrifugation, dissolved in methanol and evaporated in vacuo. The residue was dissolved in the minimum volume of a mixture of tetrahydrofuran and methanol (1:1) and poured into distilled water (200 ml, adjusted to pH 3.2 by the addition of glacial acetic acid). The preciptate was centrifuged, washed with water and dried in vacuo to give the title compound (D4) which was used without further purification.

DESCRIPTION 5

N-(9-Fluorenylmethoxycarbonyl)-13-O-methylamphotericin B (D5)

ml, 102 mg, 1.01 mmol) was added, the mixture was filtered, concentrated to ca. 10 ml and poured into diethylether/n-hexane (800 ml 1:1). The precipitated product was collected by centrifugation, washed with diethylether/ethylacetate (1:1) and dried to give the title compound (D5) as a yellow powder.

Method B

N-(9-Fluorenylmethoxycarbonyl) amphotericin B (4.99 g, 4.35 mmol) and pyridinium p-toluenesulphonate (5.04 g, 20.1 mmol) were stirred in methanol (450 ml)/tetrahydrofuran (150 ml) at room temperature for 1.5 hours. Triethylamine (2.65 g, 3.65 ml, 26.2 mmol) was added, the mixture was concentrated to 30 ml and added to saturated sodium bicarbonate solution (2 L). The precipitated product was collected by filtration, washed with water and dried to give the title compound (D5) as a yellow powder.

HPLC: Reverse phase ODS 5$\mu$ 250×4.6 column; eluant 80% methanol-20% pH 3 phosphate buffer -1 ml.min$^{-1}$; detection wavelength 350 nm; retention time: 7.6 minutes.

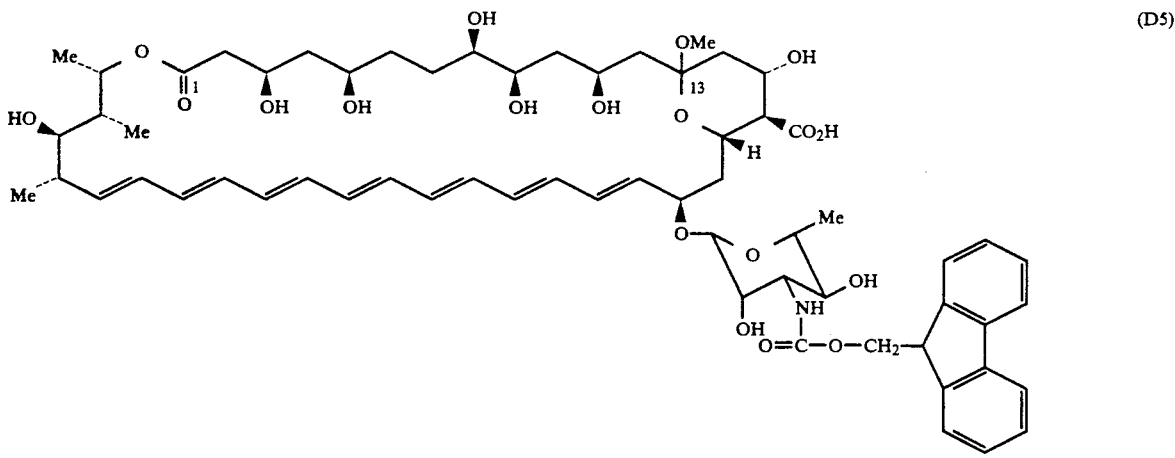

(D5)

Method A

N-(9-Fluorenylmethoxycarbonyl)amphotericin B (1.85 g, 1.61 mmol) and d-10-camphorsulphonic acid (156 mg, 0.67 mmol) were stirred in dry tetrahydrofuran (10 ml)/methanol (60 ml) at room temperature under nitrogen. After 15 minutes, triethylamine (0.14

DESCRIPTION 6

N-(9-Fluorenylmethoxycarbonyl)-13-O-methyl-3,5,8,9,11, 15,35,2',4'-nona-O-triethylsilylamphotericin B and N-(9-fluorenylmethoxycarbonyl)-3,5,8,9,11,15,35,2',4'-nona-O-triethylsilyl-13,14-anhydroamphotericin B (D6)

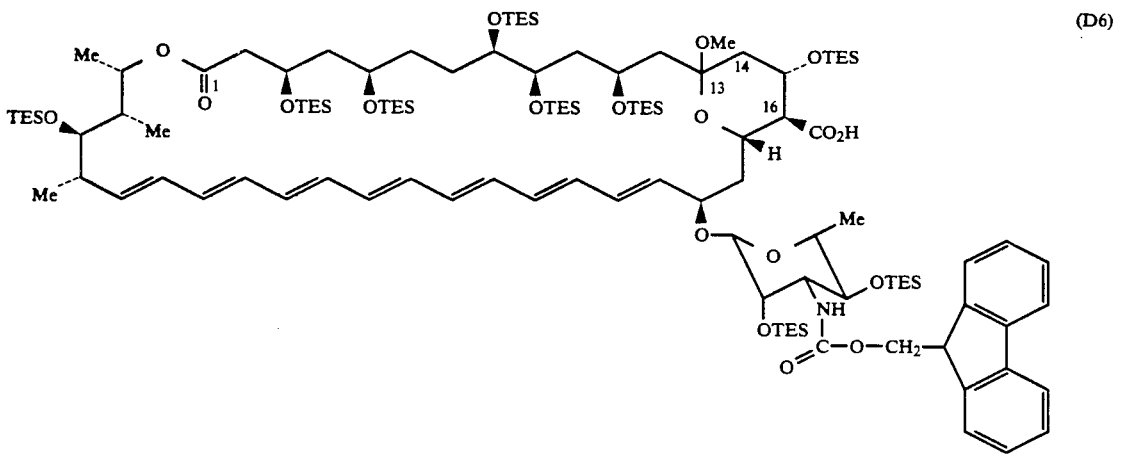

(D6)

and

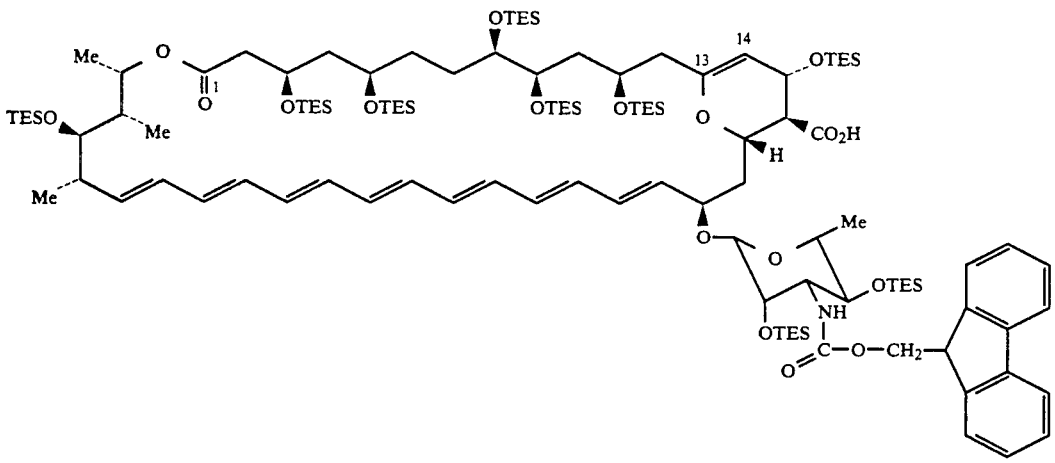

Method A

The product of Description 5 (1.52 g) was suspended in dry dichloromethane (60 ml) at 0° C. under nitrogen and 2,6-lutidine (2.55 g, 2.76 ml, 23.80 mmol) followed by triethylsilyl trifluoromethanesulphonate (4.89 g, 4.18 ml, 18.50 mmol) were added via syringe. After stirring at 0° C. for 30 minutes the solvent was evaporated and the residue was dissolved in n-hexane, filtered and the filtrate was reconcentrated to give a brown oil. Purification by column chromatography on silica gel eluting with n-hexane/ethyl acetate mixtures gave two major products.

The fractions containing the more polar 13,14-anhydro product were washed with ice/0.2 M sodium hydrogen sulphate solution to remove lutidine, dried over anhydrous magnesium sulphate, filtered and evaporated. The least polar N-(9-fluorenylmethoxycarbonyl)-13-O-methyl-3,5,8,9,11,15,35,2.,4.-nona-O-triethylsilylamphotericin B has:

Rf 0.54 (silica)-25% ethyl acetate in n-hexane. δH 400 MHz ((CD$_3$)$_2$CO): 7.88(2H, d, J 7.5 Hz), 7.70(2H, d, J 7.4 Hz, 7.43(2H, t, J 7.5 Hz), 7.34(2H, t, J 7.5 Hz), 6 63–6.10(12H, series of m), 5.97(1H, dd, J 5.3, 15.7 Hz), 5.50(1H, dd, J 9.5, 14.8 Hz), 5.37(1H, d, J 9.8 Hz), 4.75–4.62(2H, m), 4.53(1H, s), 4.51(1H, dd, J 6.4, 10.4 Hz), 4.44(1H, dt, J 4.6, 10.3 Hz). 4.35(1H, dd, J 6.5, 10.4 Hz), 4.28–4.18(2H, m), 4.14(1H, m), 4.06–3–96(2H, m), 3.90(1H, d, J 2.6 Hz), 3.86(1H dd, J 2.5, 8.8 Hz) 3.71(1H, m), 3.65–3.56(2H, m), 3.46(1H, t, J 9.1 Hz), 3.31 (1H, m), 3.14(3H, s), 2.65–2.52(2H,m), 2.44(1H, m), 2.32(1H, t, J 10.4 Hz), 2.20–1.47(15H, series of m), 1.25(3H, d, J 6.1 Hz), 1.18(3H, d, J 6.0 Hz), 1.11–0.88(87H, series of m), 0.82–0.53(54H, series of m)ppm. The carboxylic acid proton was not observed.

IR $\gamma_{max}$ (thin film): 3945, 3500–2500 (broad, weak), 2958, 2915, 2880, 1733 (shoulders at 1720, 1710), 1509, 1459, 1413, 1379, 1308, 1237, 1190, 1108, 1077, 1004, 901, 860, 830, 739 cm$^{-1}$. Mass spectrum: FAB (3-NOBA matrix) observed mass MH$^+$ 2187. Calculated for C$_{117}$H$_{211}$NO$_{19}$Si$_9$H$^+$, 2187.

The more polar product N-(9-fluorenylmethoxycarbonyl)-3,5,8,9,11,15,35,2',4'-nona-O-triethylsilyl-13,14anhydroamphotericin B has:

Rf 0.40 (silica)-25% ethyl acetate in n-hexane. δH 400MHz ((CD3)2CO) 7.88(2H, d, J 7.5 Hz), 7.70(2H, d, J 7.5 Hz), 7.43(2H, t, J 7.4 Hz), 7.34(2H, t, J 7.4 Hz), 6.56–6.11(12H, series of m), 5.99(1H, dd, J 6.0, 15.4 Hz), 5.55(1H, dd, J 9.4, 14.9 Hz), 5.34(1H, d, J 9.9 Hz), 4.80(1H, d, J 8.7 Hz), 4.73–4.60(2H, m), 4.63(1H, s), 4.59(1H, s), 4.50(1H, dd, J 6.5, 10.4 Hz), 4.35(1H, dd, J 6.5, 10.4 Hz), 4.32–4.17(3H, m), 4.12((1H, m), 4.01(1H, m), 3.90(1H, d, J 2.7 Hz) 3.85(1H, dd, J 2.8, 8.7 Hz), 3.80–3.66(2H, m), 3.61(1H, dt, J 2.7, 9.7 Hz), 3.45(1H, t, J 9.1 Hz), 3.34(1H, m), 2 64(1H, dd, J 8.7, 10.8 Hz), 2.61–2.50(2H, m), 2.43(1H, m), 2.40–2.28(1H, m), 2.24–2.15(1H, m), 2.08–1.88(5H, series of m), 1.83–1.47(6H, series of m), 1.25(3H, d, J 6.1 Hz), 1.18(3H, d, J 6.0 Hz), 1.10–0.88(87H, series of m), 0.77–0.56(54H, series of m)ppm. The carboxylic acid proton was not observed.

IR γmax (thin film) : 3445, 3500–2500 (broad, weak), 1737 (shoulder at 1720), 1680, 1510, 1461, 1416, 1380, 1310, 1240, 1192, 1169, 1080, 1007, 977, 740, 672 cm$^{-1}$. Mass spectrum FAB (3-NOBA matrix) Observed mass MH+2155.5. Calculated for $C_{116}H_{207}NO_{18}Si_9H^+$, 2155.

Method B

N-(9-Fluorenylmethoxycarbonyl)-13-O-methylamphotericin B (D5) (4.97 g, 4.3mmol) was suspended in dry n-hexane (150 ml) at 0° C. under nitrogen and treated with 2,6-lutidine (8.3 g, 8.9 ml, 77 mmol) followed by triethylsilyl trifluoromethanesulphonate (15.8 g, 13.6 ml, 60 mmol). After stirring at 0° C. for 2hrs further batches of 2,6-lutidine (4.5 ml) and triethylsilyl trifluoromethanesulphonate (6.8 ml) were added in two portions 15 minutes apart. Stirring was continued for a further 1 hr and the mixture was filtered and concentrated in vacuo. Purification by chromatography on silica gel (eluting with ethyl acetate/n-hexane mixtures) gave, as a yellow/orange foam, a single major product identified as the least polar product of Method A.

DESCRIPTION 7

N-(9-Fluorenylmethoxycarbonyl)-13-O-methyl-3,5,8,9,11, 15,35,2′,4′-nona-O-triethylsilylamphotericin B (2-pyridylthio)ester (D7)

The 13-O-methyl product of Description 6 (823 mg, 0.38 mmol) was stirred at 0° C. in dry diethyl ether (15 ml) and treated with triethylamine (50 mg, 0.07 ml, 0.49 mmol) followed by 2-thiopyridyl chloroformate (105 mg, 3 ml of 35 mg/ml solution in dichloromethane). After stirring at 0° C. for 30 minutes, the mixture was diluted with diethyl ether (80 ml), dried over anhydrous magnesium sulphate, filtered and evaporated in vacuo. Purification by flash chromatography on silica gel eluting with 10% ethyl acetate in n-hexane gave the title compound as a yellow/orange foam.

Rf: 0.45 (silica), 15% ethyl acetate in n-hexane. δH 270 MHz ((CD$_3$)$_2$CO) 8.73(1H, d, J 5 Hz), 7.95(1H, dt, J 7.5, 2 Hz), 7.88(2H, d, J 7.2 Hz), 7.73(1H, d, J 7.5 Hz), 7.71(2H, d, J 7 Hz), 7.50–7.25(5H, m), 6.70–6.08(12H, series of m). 5.97(1H, dd. J 5.5, 15 Hz). 5.50(1H, dd, J 9.6. 15 Hz). 5.30(1H. d. J 9.6 Hz). 4.78(1H. m). 4.65(1H, m), 4.62(1H, s), 4.56–4.42(2H, m), 4.38–3.96(6H, series of m), 3.92(1H, d, J 3 Hz), 3.87(1H, dd, J 9, 3 Hz), 3.77–3.55(3H, m), 3.50–3.35(2H, m), 3.13(3H, s), 2.77(1H, t, J 9 Hz), 2.59(2H, d, J 6.4 Hz), 2.44(1H, m), 2.32(1H, dd, J 6.4, 14 Hz), 2.15–1.40(14H, series of m), 1.23(3H, s, J 5 Hz), 1.18(3H, s, J 6 Hz), 1.15–0.86(87H, m), 0.85–0.45(54H, series of m)ppm.

IR γ$_{max}$ (thin film) : 3459, 2965, 2920, 2888, 1737 (shoulder at 1710), 1578, 1510, 1460, 1418, 1382, 1312, 1241, 1115, 1080, 1010, 740 cm$^{-1}$. Mass spectrum : FAB(3-NOBA/Na matrix). Observed mass MNa+2302, calculated for $C_{122}H_{214}N_2O_{18}Si_9SNa^+$, 2302.

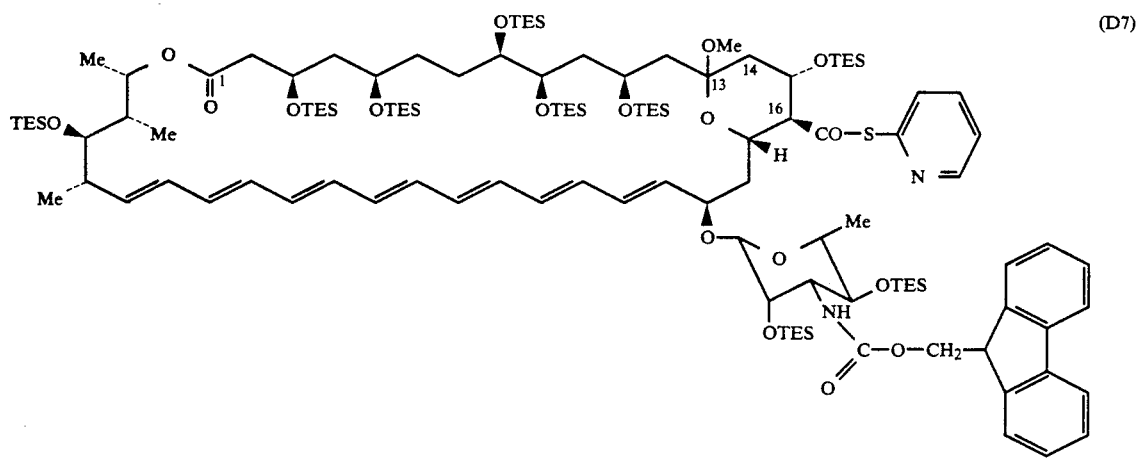

(D7)

DESCRIPTION 8

N-(9-Fluorenylmethoxycarbonyl)-3,5,8,9,11,15,35,2',4'-nona-O-triethylsilyl-13,14-anhydroamphotericin B (2-pyridylthio)ester (D8)

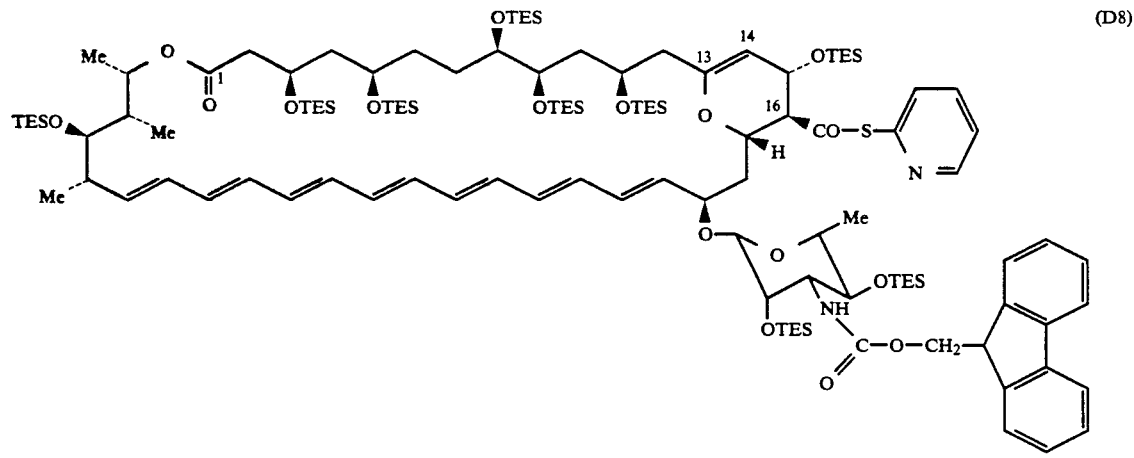

N-(9-Fluorenylmethoxycarbonyl)-3,5,8,9,11,15,35,2',4'-nona-O-triethylsilyl-13,14-anhydroamphotericin B (460 mg, 0.21 mmol) was treated as in Description 7 with triethylamine (24 mg, 0.03 ml, 0.24 mmol) and 2-thiopyridyl chloroformate (52 mg, 1.50 ml of 35 mg/ml solution in dichloromethane) in diethyl ether (12 ml). Work-up and purification gave the title compound (D8) as a yellow glassy solid.

Rf : 0.28(silica), 10% ethyl acetate in n-hexane. 6H 270MHz ((CD$_3$)2CO) : 8.73(1H, d J 4 Hz), 7.94(1H, dt, J 8, 2 Hz), 7.88(2H, d, J 8 Hz), 7.74(1H, d, J 8 Hz), 7.71(2H, d J 8 Hz), 7.50-7.27(5H, m), 6.65-6.15(12H, series of m), 6.0(1H, dd, J 15, 7 Hz), 5.65(1H, dd, J 9, 14 Hz), 5.32(1H, d, J 10 Hz), 4.90-4.60(2H, m), 4.74(1H, s), 4.66(1H, s), 4.51(1H, dd, J 10, 7 Hz), 4.40-3.65(10H, series of m), 3.93(1H, d, J 3 Hz), 3.86(1H, dd, J 8, 2 Hz), 3.50-3.35(2H, m), 3.03(1H, dd, J 11, 9 Hz), 2.65-1.40(16H, series of m), 1.23(3H, d, J 6 Hz), 1.18(3H, d, J 6 Hz), 1.16-0.85(87H, series of m), 0.85-0.45(54H, series of m)ppm IR γ$_{max}$ (thin film) : 3457, 3020, 2962, 2920, 2883, 1736, 1705, 1679, 1577, 1508, 1460, 1420, 1383, 1311, 1240, 1192, 1169, 1080, 1007, 836, 730 cm$^{-1}$ Mass spectrum: FAB(3-NOBA/Na matrix) observed mass MNa$^+$ 2270, calculated for C$_{121}$H$_{210}$N$_2$O$_{17}$Si$_9$S Na$^+$, 2270.

DESCRIPTION 9

N-(9-Fluorenylmethoxycarbonyl)-16-decarboxy-16-hydroxy-methyl-13-O-methyl-3,5,8,9,11,15,35,2',4'-nona-O-triethylsilylamphotericin B (D9)

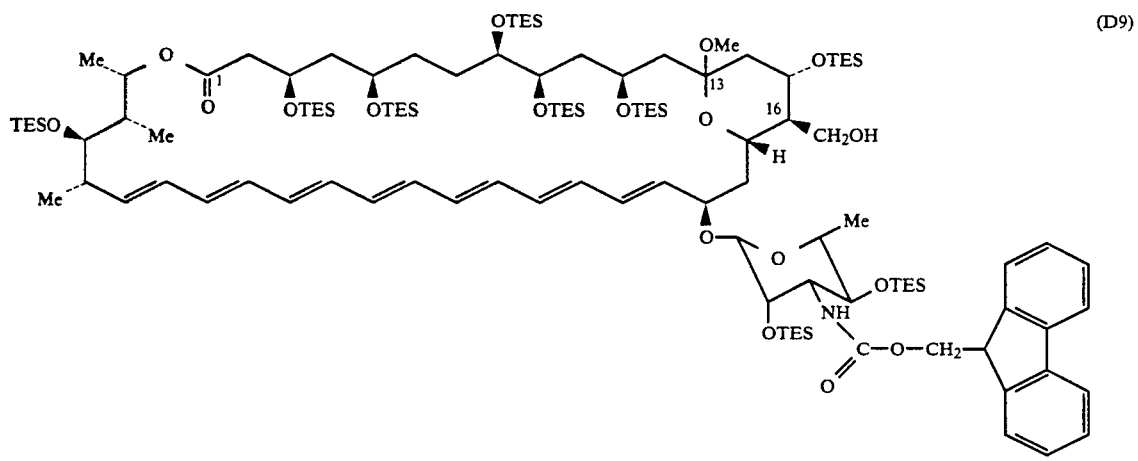

Method A

N-(9-Fluorenylmethoxycarbonyl)-13-O-methyl-3,5,8,9,11, 15,35,2',4'-nona-O-triethylsilylamphotericin B (2-pyridylthio)ester (D7) (61 mg, 0.03 mmol) was stirred between −10° C. and room temperature in dry tetrahydrafuran (2 ml) and treated with lithium borohydride (0.9 ml of 0.57 M solution in tetrahydrofuran, 0.51 mmol, added in three portions over 30 minutes). After stirring overnight at room temperature, more lithium borohydride (6.0 mg, 0.28 mmol) was added and stirring was continued for a further 3 hours. The mixture was cooled to −78° C., quenched with saturated ammonium chloride solution and allowed to reach room temperature. The product was extracted into diethyl ether and the organic extracts were dried over anhydrous magnesium sulphate, filtered and concentrated. Purification by flash chromatography on silica gel eluting with 0-2% diethyl ether in dichloromethane gave the title compound (D9) as a yellow glass.

Method B

N-(9-Fluorenylmethoxycarbonyl)-13-O-methyl-3,5,8,9,11, 15,35,2',4'-nona-O-triethylsilylamphotericin B (2-pyridylthio)ester (D7) (3.26 g, 1.43 mmol) was stirred in diethyl ether (60 ml), under nitrogen at room temperature and treated with lithium borohydride (0.150 g, 6.89 mmol). After 2hrs the mixture was cooled to 0° C., saturated ammonium chloride solution was added and the mixture was stirred vigorously for a few minutes. The product was extracted into diethyl ether and the combined organic extracts were dried over anhydrous magnesium sulphate, filtered and then concentrated in vacuo. Purification by flash chromatography on silica gel (eluting with diethyl ether/dichloromethane mixtures) gave the title compound (D9) as a yellow glassy solid.

Rf: 0.44 (silica), 2% diethylether in dichloromethane. $\delta H$ 400 MHz ((CD$_3$)$_2$CO) 7.87(2H, d, J 7.5 Hz), 7.69(2H, d, J 7.4 Hz), 7.43(2H, t, J 7.4 Hz), 7.34((2H, t, J 7.4 Hz), 6.54–6.10(12H, series of m), 6.06(1H, dd, J 15.4 6.1 Hz), 5.51(1H, dd, J 14.8, 9.7 Hz), 5.37(1H, d, J 9.8 Hz), 4.78(1H, s), 4.78–4.62(2H, m), 4.48(1H, dd, J 10.4, 6.5 Hz), 4.34(1H, dd, J 10.4, 6.5 Hz), 4.30–4.08(4H, m), 4.05–3.76(6H, m), 3.74–3.58(3H, m), 3.47(1H, t, J 9.0 Hz), 3.35(1H, m), 3.12(3H, s), 2.63–2.50 (2H, m), 2.48–2.36(2H, m), 2.12(1H, dd, J 12.3, 4.4 Hz), 2.07–1.25(14H, series of m), 1.25(3H, d, J 6.1 Hz), 1.18(3H, d, J 6.0 Hz), 1.14–0.85(87H, series of m), 0.80–0.53(54H, series of m)ppm. The OH proton was not observed.

IR $\gamma_{max}$ (thin film): 3600–3300 (weak, broad), 3450, 2915, 2879, 1737, 1510, 1461, 1414, 1380, 1309, 1240, 1193, 1110, 1078, 1007, 905, 839, 740, 725, 674 cm$^{-1}$. Mass spectrum: FAB(3-NOBA/Na matrix) observed mass MNa$^+$ 2195, calculated for C$_{117}$H$_{213}$NO$_{18}$Si$_9$Na$^+$, 2195.

DESCRIPTION 10

N-(9-Fluorenylmethoxycarbonyl)-16-decarboxy-16-formyl-13-O-methyl-3,5,8,9,11,15,35,2',4'-nona-O-triethylsilylamphotericin B (D10)

A mixture of dry dimethyl sulphoxide (109 mg, 0.09 ml, 1.30 mmol) and tetramethylurea (151 mg, 0.16 ml, 1.30 mmol) in dry dichloromethane (4 ml) was stirred at −78° C. under nitrogen and trifluoroacetic anhydride (136 mg, 0.092 ml, 0.65 mmol) was added dropwise via syringe. After 15 minutes the alcohol of Description 9 (141 mg, 0.07 mmol) in dichloromethane (4 ml) was added via canula. The mixture was stirred for 1.5 hrs between −78° C. and −60° C. before the dropwise addition of triethylamine (132 mg, 0.18 ml, 1.30 mmol). After stirring for a further 15 minutes at −78° C., the mixture was allowed to reach room temperature before quenching with saturated sodium bicarbonate solution. The product was extracted into diethyl ether and the combined organic extracts were dried over anhydrous magnesium sulphate, filtered and evaporated. Flash chromatography on silica gel eluting with 1% diethylether in dichloromethane gave the title compound as a yellow/orange glassy solid.

Rf: 0.72 (silica), 2% diethylether in dichloromethane. $\delta C$ 67.8 MHz ((CD$_3$)$_2$CO) 204.2, 170.5, 156.3, 145.1, 142.2, 139.3, 135.6, 135.4, 135.0, 134.7, 134.2, 133.6, 132.5, 132.4, 132.2, 131.5, 131.3, 130.6, 128.5, 127.8, 125.8, 125.7, 120.8, 101.4, 98.6, 76.7, 76.3, 76.0, 74.5, 74.0, 73.5, 73.2, 71.1, 67.4, 67.3, 67.2, 65.2, 62.9, 58.1, 48.3, 48.0, 45.8, 44.3, 43.4, 42.3, 41.4, 40.8, 36.3, 35.6, 27.5, 20.0, 19.3, 19.0, 11.2, 7.64, 7.61, 7.5, 7.3, 7.1, 6.8, 6.6, 6.4, 6.2, 5.9, 5.8, 5.6, 5.4 ppm.

IR $\gamma_{max}$ (thin film): 3452, 2957, 2912, 2879, 2730 (weak), 1733, 1503, 1459, 1412, 1378, 1309, 1240, 1190, 1110, 1079, 1007, 977, 903, 862, 833, 740, 671 cm$^{-1}$. Mass spectrum: FAB (3-NOBA matrix) Observed mass M$^+$ 2170, calculated for C$_{117}$H$_{211}$NO$_{18}$Si$_9$, 2170.

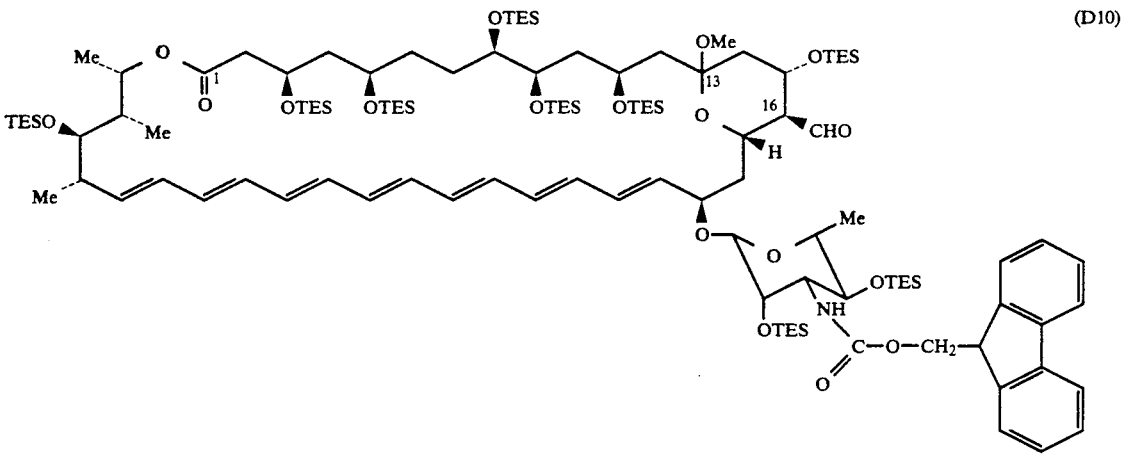

(D10)

DESCRIPTION 11

N-(9-Fluorenylmethoxycarbonyl)-16-decarboxy-16-hydroxymethyl-3,5,8,9,11,15,35,2',4'-nona-O-triethylsilyl-13, 14-anhydroamphotericin B (D11)

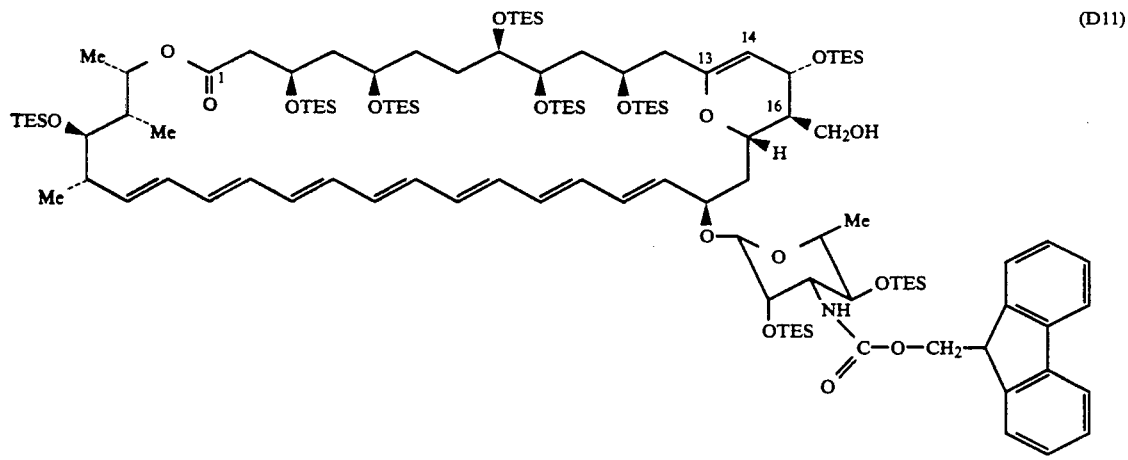

A mixture of N-(9-fluorenylmethoxycarbonyl)-3,5,8,9,11, 15,35,2',4'-nona-O-triethylsilyl-13,14-anhydroamphotericin B (2-pyridylthio) ester (D8) (282 mg, 0.13 mmol) and lithium borohydride (16.40 mg, 0.75 mmol) was stirred in dry tetrahydrofuran (10 ml) under nitrogen at room temperature. After 18 hours the mixture was cooled to −78° C., quenched with saturated ammonium chloride solution and allowed to reach room temperature. The product was extracted into diethyl ether and the combined extracts were dried over anhydrous magnesium sulphate, filtered and evaporated. Purification by flash chromatography on silica gel, eluting with 1–3% diethyl ether in dichloromethane gave the title compound as a yellow glass.

Rf: 0.40 (silica), 1% diethyl ether in dichloromethane.
$\delta$H 270 MHz ((CD$_3$)$_2$CO) 7.88(2H, d, J 7.4 Hz), 7.70(2H, d, J 7.4 Hz), 7.46–7.34(4H, m), 6.60–6.05(13H, series of m), 5.55(1H, dd, J 9, 14 Hz), 5.39(1H, d, J 10.6 Hz), 4.75–3.65(18H, series of m, including 4.73(1H,s), 4.65(1H, d, J 2 Hz), 3.93(1H, d, J 3 Hz)), 3.60(1H, dt, J 3.0, 9.5 Hz), 3.46(1H, t, J 9.0 Hz), 3.31(1H, m) 2.58(2H, m), 2.50–1.45(15H, series of m), 1.25(3H, d, J 6.1 Hz), 1.18(3H, d, J 6.7 Hz), 1.15–0.80(87H, series of m), 0.75–0.45(54H, series of m)ppm. The OH proton was not observed.

IR $\gamma_{max}$ (thin film): 3600–3300 (broad, weak), 3440, 2950, 2902, 2870, 1726, 1668, 1505, 1455, 1408, 1372, 1302, 1233, 1187, 1161, 1073, 1000, 898, 857, 833, 805, 732, 720, 667 cm$^{-1}$. Mass spectrum : FAB(3-NOBA/Na matrix) observed mass MNa+ 2163, calculated for C$_{116}$H$_{209}$NO$_{17}$Si$_9$Na+, 2163.

DESCRIPTION 12

N-Trifluoroacetylamphotericin B (D12)

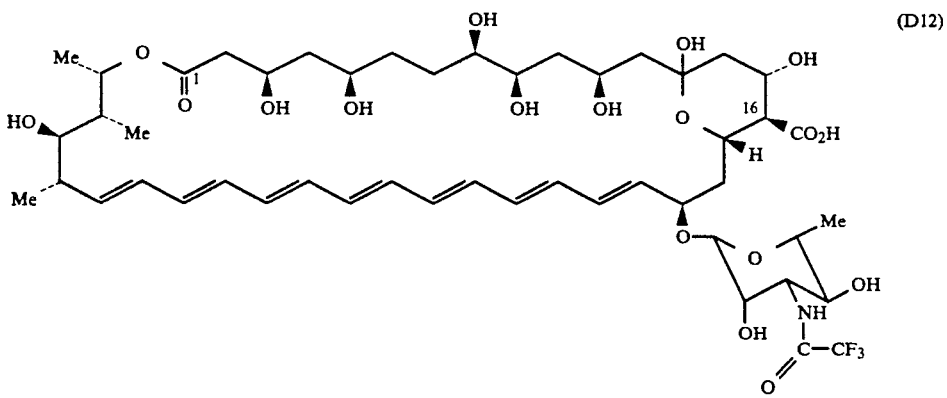

A mixture of amphotericin B (2.20 g, 2.38 mmol), ethyl trifluoroacetate (0.51 g, 0.43 ml, 3.57 mmol)) and diisopropylethylamine (0.46 g, 0.62 ml, 3.57 mmol) in dry dimethylformamide (100 ml)/methanol (10 ml) was stirred at room temperature under nitrogen. After stirring overnight, the mixture was poured into diethylether (4 L) containing glacial acetic acid (ca. 1 ml). The precipitated solid was collected by filtration, washed with diethyl ether and ethyl acetate, and dried to give the title compound (D12) as a brown powder. HPLC : Reverse phase ODS 5% 250×4.6 mm column; eluant 78% methanol-22% pH 3 phosphate buffer - 1 ml.min$^{-1}$; detection wavelength 350 mm; retention time 7.9 minutes $\delta$H 270 MHz(d$_4$-methanol/d$_5$-pyridine 1:1) 6.75–6.23(13H series of m), 5.75–5.40(2H, m, partially masked by solvent peaks), 5.0–4.60(5H, series of m), 4.49(1H, m), 4.37(1H, dd, J 3.0, 10.5 Hz), 4.27(1H, d, J 3.0 Hz), 4.05–3.80(3H, m), 3.57(1H, m), 3.45–3.30(2H, m), 2.70–2.30(6H, series of m). 2.28–1.30(13H, series of m), 1.43(3H, d, J 6.3 Hz), 1.36(3H, d, J 6.6 Hz), 1.25(3H, d, J 6.3 Hz), 1.18(3H, d, J 7.2 Hz),ppm. IR $\gamma_{max}$ (KBr disc) : 3400 (broad), 2920, 1720, 1552, 1379, 1323, 1172, 1063, 1010, 883, 847, 795 cm$^{-1}$.

DESCRIPTION 13

N-Trifluoroacetyl-13-O-methyl-3,5,8,9,11,15,35,2',4'-nona-O-triethylsilylamphotericin B and N-trifluoroacetyl-3,5,8,9,11,15,35,2',4'-nona-O-triethylsilyl-13,14-anhydroamphotericin B (D13)

The yellow powder was suspended in dry dichloromethane (60 ml) at 0° C. under nitrogen and 2,6-lutidine (2.51 g, 2.72 ml, 23.40 mmol), followed by triethylsilyl trifluoromethanesulphonate (4.77 g, 4.08 ml, 18.00 mmol) were added via syringe. After stirring at 0° C. for 30 minutes the solvent was evaporated and the residue

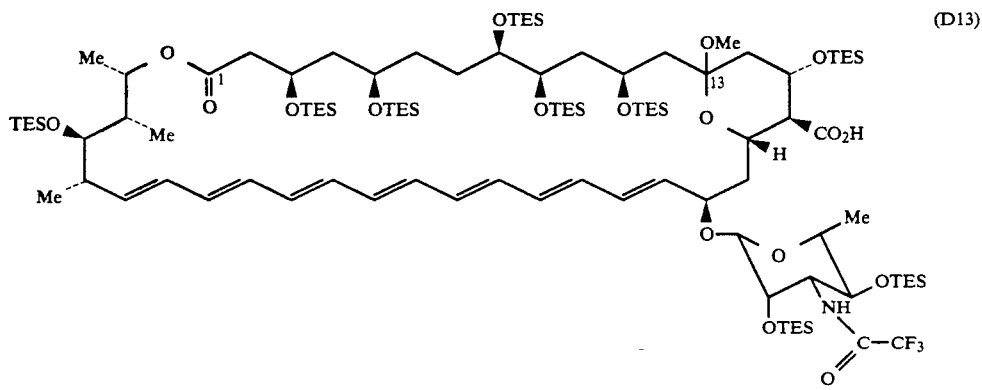

(D13)

and

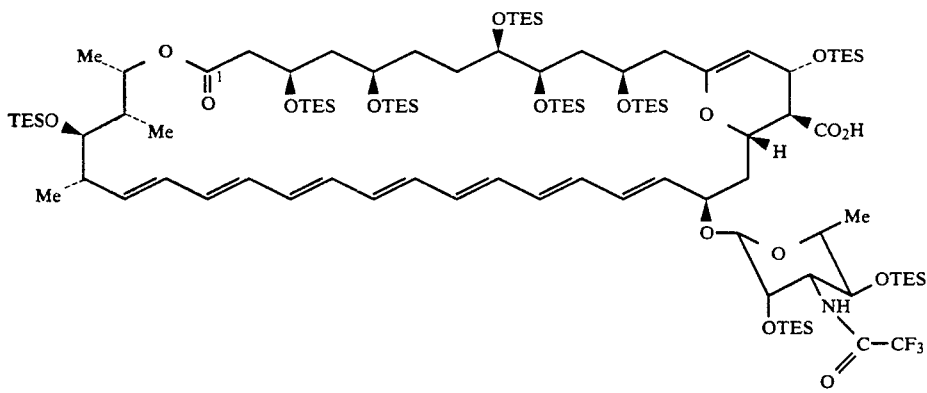

N-Trifluoroacetylamphotericin B (D12) (1.99 g, 1.96 mmol) and d-10-camphorsulphonic acid (180 mg, 0.77 mmol) were stirred in dry tetrahydrofuran (10 ml)/methanol (60 ml) at room temperature under nitrogen. After 15 minutes, triethylamine (118 mg, 0.16 ml, 1.16 mmol) was added, the solution was concentrated to ca. 10 ml and added to diethylether (2 L). The precipitated product was collected by filtration, washed with diethyl ether and ethyl acetate and dried to give N-trifluoroacetyl-13-O-methylamphotericin B as a yellow powder. HPLC: Same conditions as in Description 12; retention time 5.1 minutes.

was dissolved in n-hexane, filtered and the filtrate was reconcentrated. Purification by column chromatography on silica gel eluting with n-hexane/ethyl acetate mixtures gave two major products.

a) 13-0-methyl derivative Rf 0.33 (silica)-10% ethyl acetate in n-hexane.

b) 13,14-anhydro derivative Rf 0.23 (silica)-10% ethyl acetate in n-hexane.

DESCRIPTION 14

N-Trifluoroacetyl-13-O-methyl-3.5,8,9,11,15,35,2',4'-nona-O-triethylsilylamphotericin B (2-pyridylthio)ester (D14)

DESCRIPTION 15

N-Trifluoroacetyl-3,5,8,9,11,15,35,2',4'-nona-O-triethylsilyl-13,14-anhydroamphotericin B (2-pyridylthio)ester (D15)

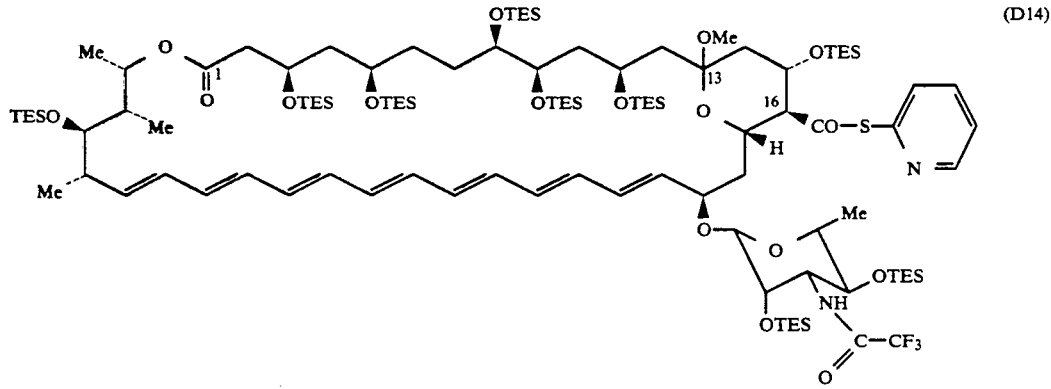

(D14)

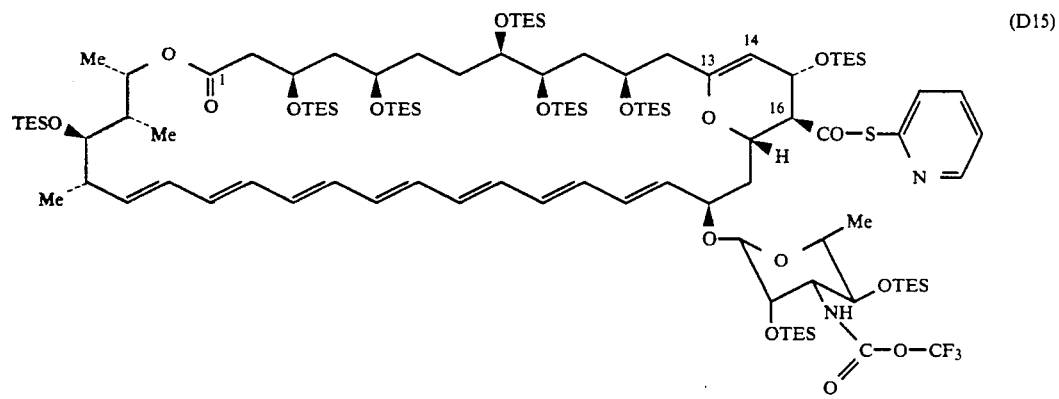

(D15)

The crude sample of N-trifluoroacetyl-13-O-methyl-3,5, 8,9,11,15,35,2',4'-nona-O-triethylsilylamphotericin B (1.16 g) prepared in Description 13 was treated as in Description 7 with triethylamine (64 mg, 0.09 ml, 0.63 mmol) and 2-thiopyridyl chloroformate (148 mg, 4.20 ml of 35 mg/ml solution in dichloromethane, 0.86 mmol) in diethyl ether (20 ml). Work up and purification gave the title compound (D14) as a yellow foam.

Rf 0.44 (silica)-10% ethyl acetate in n-hexane. δH 400 MHz ((CD$_3$)$_2$CO) : 8.73(1H, dd, J 1.0, 4.8 Hz), 7.93(1H, dt, J 1.9, 7.8 Hz), 7.73(1H, d, J 7.9 Hz), 7.41(1H, ddd, J 1.0, 4.8, 7.6 Hz), 7.21(1H, d, J 9.1 Hz partially deuterated), 6.61–6.11(12H, series of m), 5.98(1H dd, J 5.6, 15.7 Hz), 5.50(1H, dd, J 9.6, 4.7 Hz), 4.82(1H, m), 4.71(1H, s), 4.69(1H, m), 4.48(1H, dt, J 4.5, 10.3 Hz), 4.24(1H, m), 4.14(1H, m), 4.10–3.95(4H, m), 3.84(1H, dd, J 2.6, 8.8 Hz), 3.73–3.60(3H, m, including t, J 8.8 Hz at 3.67), 3.52(1H, dq, J 6.3, 8.5 Hz), 3.15(3H, s), 2.73(1H, t, J 10.1 Hz), 2.57(2H, d, J 6.8 Hz), 2.44(1H, m), 2.32(1H, dd, J 6.8, 14.9 Hz), 2.17–1.60(13H, series of m), 1.51(1H, m), 1.28(3H, d, J 6.2 Hz), 1.18(3H, d, J 6.0 Hz), 1.14–0.90(87H, series of m), 0.83–0.57(54H, series of m)ppm. Mass spectrum : FAB(3-NOBA/Na matrix) observed mass MNa$^+$ 2175±1, calculated for C$_{109}$H$_{203}$N$_2$O$_{17}$Si$_9$SF$_3$Na$^+$, 2176.

The crude sample of N-trifluoroacetyl-3,5,8,9,11,15,35, 2',4'-nona-O-triethylsilyl-13,14-anhydroamphotericin B (697 mg) of Description 13 was stirred at 0° C. in dry diethylether (10 ml) and treated with triethylamine (33 mg, 0.05 ml, 0.33 mmol) followed by 2-thiopyridyl chloroformate (77 mg, 2.2 ml of 35 mg/ml solution in dichloromethane, 0.44 mmol). After stirring at 0° C. for 30 minutes another 0.01 ml of triethylamine and 0.5 ml of 2-thiopyridyl chloroformate solution were added and stirring was continued for a further 20 minutes. The mixture was diluted with diethyl ether (100 ml), dried over anyhydrous magnesium sulphate, filtered and evaporated. Purification by flash chromatography on silica gel eluting with 10% ethyl acetate in n-hexane gave the title compound (D15) as a yellow glassy solid.

Rf : 0.89 (silica)- 15% ethyl acetate in n-hexane. δH 400 MHz ((CD$_3$)$_2$CO) : 8.72(1H, ddd, J 0.%, 1.9, 4.8 Hz), 7.94(1H, dt, J 1.9, 7.7 Hz), 7.74(1H, dt, J 0.9, 7.9 Hz), 7.45(1H ddd, J 1.1, 4.8, 7.6 Hz}, 7.27(1H. d, J 9.2 Hz), 6.55–6.11(12H, series of m), 6.01(1H, dd, J 6.4, 15.4 Hz), 5.56(1H, dd, J 9.3, 14.8 Hz), 4.83–4.79(1H, m), 4.82(1H, s), 4.77(1H, m), 4.69(1H, m), 4.67(1H, s), 4.35(1H, ddd, J 2.1, 7.4, 10.5 Hz), 4.22(1H, m), 4.16–4.06(2H, m), 4.05(1H, d, J 3.1 Hz), 4.01(1H, m), 3.85(1H, dd, J 2.8, 8.6 Hz), 3.80–3.69(2H, m), 3.68(1H, t, J 8.9 Hz), 3.52(1H, dq, J 6.2, 8.6 Hz), 3.04(1H, dd, J 8.6, 10.7 Hz), 2.58(1H, dd, J 5.8, 7.1 Hz, A of ABX system), 2.52(1H, dd, J 7, 17.1 Hz, B of ABX system), 2.43(1H, m), 2.40–2.30(2H, m), 2.12–1.88(5H, series of m), 1.82–1.58(5H, series of m), 1.51(1H, m), 1.27(3H, d, J 6.2 Hz), 1.19(3H, d, J 6.0 Hz), 1.10–0.92(87H, series of m), 0.77–0.59(54H, series of m)ppm.

IR $\gamma_{max}$ (thin film) : 3430, 2958, 2916, 2880, 1737, 1703, 1676, 1574, 1529, 1460, 1416, 1379, 1298, 1239, 1187, 1167, 1075, 1006, 837, 740, 672 cm$^{-1}$. Mass spectrum: FAB(3-NOBA/Na matrix) observed mass 144, calculated for $C_{108}H_{199}N_2O_{16}Si_9SF_3Na^{30}$, 2144.

DESCRIPTION 16

N-Trifluoroacetyl-16-acetyl-16-decarboxy-13-O-methyl-3,5,8,9,11,15,35,2′,4′-nona-O-triethylsilylamphotericin B (D16)

trated. Purification by flash chromatography on silica gel, eluting with dichloromethane gave the title compound (D16) as a yellow glass Rf : 0.46 (silica), dichloromethane. δH 270MHz ((CD$_3$)$_2$CO) : 7.40(1H, d, J 9.1 Hz), 6.50–6.07(12H, series of m), 6.0(1H, dd, J 6.3, 15.4 Hz), 5.51(1H, dd, J 9, 14 Hz), 4.76–4.55(3H, m, 1 including s at 4.63), 4.33(1H, dt, J 5, 9.6 Hz), 4.25(1H, m), 4.20–3.90(5H, series of m), 3.85(1H, dd, J 3, 8.8 Hz), 3.80–3.57(3H, m), 3.42(1H, dq, J 6.3, 8.2 Hz), 3.14(3H, s), 2.69(1H, t, J 10.3 Hz), 2.58(2H, d, J 6.3 Hz), 2.44(1H, m), 2.28(3H, s), 2.14–1.44(15H, series of m), 1.28(3H, d, J 6.1 Hz), 1.18(3H, d, J 6.1 Hz), 1.14–0.86(87H, series of m), 0.83–0.50(54H, series of m)ppm.

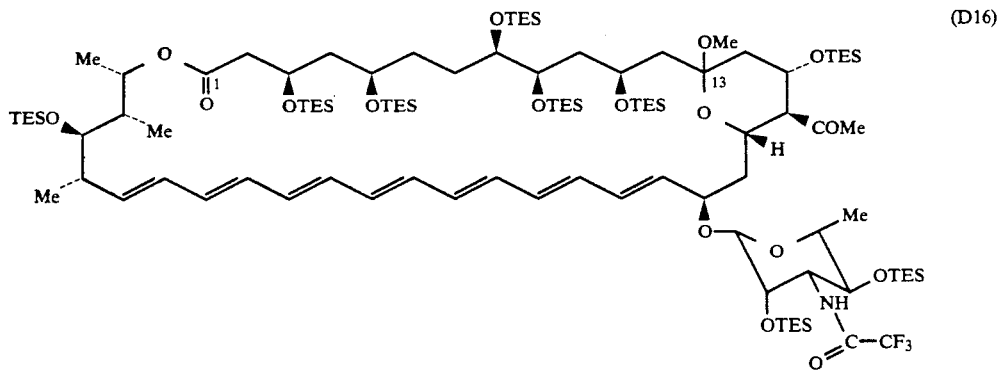

The pyridylthio ester of Description 14 (626 mg, 0.31 mmol) was stirred at 0° C. in dry tetrahydrofuran (10 ml) under nitrogen and treated with methylmagnesium bromide (1.02 ml of 3 M solution in diethyl ether, 3.1 mmol). Further batches of methylmagnesium bromide (2.0 mls in 3 batches over 4.5 hours) were added and the mixture was allowed to reach room temperature after 3 hours. After 5 hours in total, water was added and the product was extracted into diethyl ether. The combined extracts were washed with saturated brine, dried over anhydrous magnesium sulphate, filtered and concentrated.

IR $\gamma_{max}$ (thin film) : 3425, 2955, 2910, 2875, 1731, 1710, 1525, 1458, 1411, 1376, 1305, 1236, 1160, 1080 (broad), 1001, 899, 864, 830, 739, 669 cm$^{-1}$.

DESCRIPTION 17

N-Trifluoroacetyl-16-benzoyl-16-decarboxy-3,5,8,9,11,15,35,2′,4′-nona-O-triethylsilyl-13,14-anhydroamphotericin B and
16-benzoyl-16-decarboxy-3,5,8,9,11,15,35, 2′,4′-nona-O-triethylsilyl-13,14-anhydroamphotericin B (D17)

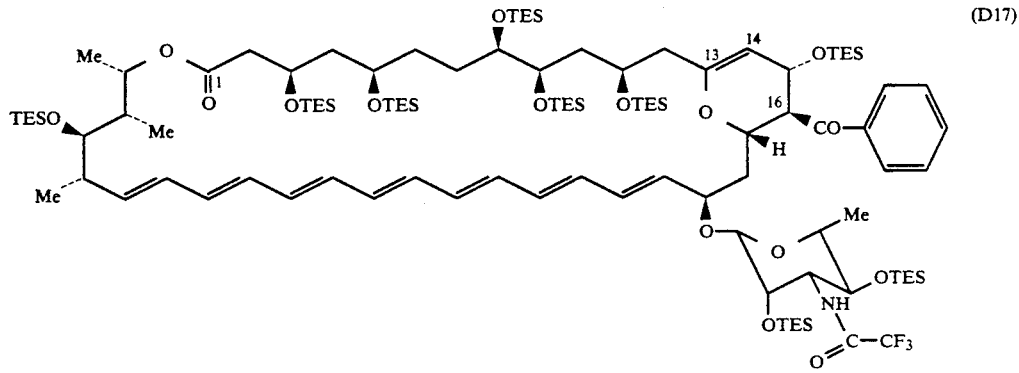

and

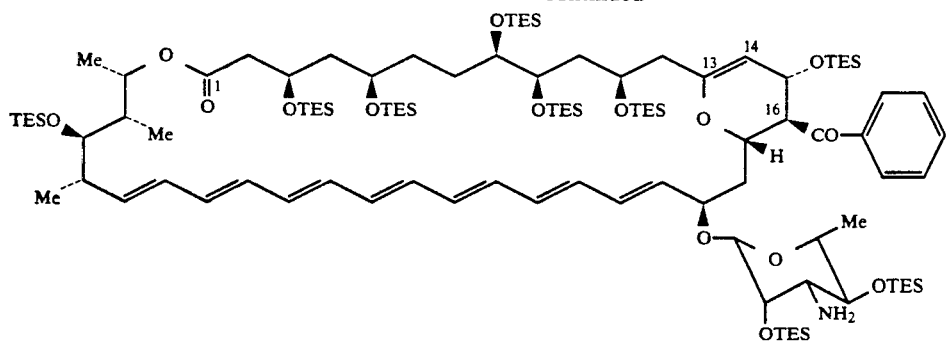

The pyridylthio ester of Description 15 (529 mg, 0.24 mmol) was stirred at 0° C. in dry tetrahydrofuran (15 ml) under nitrogen and phenylmagnesium bromide (0.79 ml of 3M solution in diethyl ether, 2.35 mmol) was added via syringe. After 30 minutes another 0.30 ml of phenylmagnesium bromide solution was added and stirring was continued for a further 1.5 hours. Water was added and the product was extracted into diethyl ether. The combined extracts were washed with saturated brine, dried over anhydrous magnesium sulphate, filtered and evaporated. Purification by column chromatography on silica gel eluting with n-hexane/ethyl acetate and n-hexane/dichloromethane mixtures gave two major The least polar N-trifluoroacetyl derivative has: Rf : 0.71 (silica), 15% ethyl acetate in n-hexane. δH 270 MHz ((CD$_3$)$_2$CO) 8.12(2H, d, J 6.9 Hz), 56(3H, m), 7.37(1H, d, J 9.1 Hz), 6.57–6.09(12H, series of m), 5.90(1H, dd, J 6.6, 15.7 Hz), 5.54(1H, dd, J 10, 15 Hz), 4.83(1H, d, J 8.2 Hz), 4.73(1H, s), 4.66(1H, m), 4.42(2H, m), 4.27–3.66(10H, series of m), 3.60(1H, t, J 8.9 Hz), 3.05(1H, m), 2.66–2.33(4H, m), 2.10–1.43(12H, series of m), 1.23–0.88(93H, series of m), 0.88–0.35(54H, series of m)ppm. IR γ$_{max}$ (thin film) : 3435, 2957, 2915, 2880, 1737, 1675, 1599, 1528, 1460, 1413, 1379, 1296, 1240, 1166, 1071, 1005, 897, 857, 839, 730, 670 cm$^{-1}$. Mass spectrum: FAB(3-NOBA/Na matrix) observed mass MNa$^+$ 2112±1, calculated for C$_{109}$H$_{200}$NO$_{16}$Si$_9$F$_3$Na$^{30}$, 2111.

The more polar free amino derivative has: Rf 0.38 (silica), 15% ethyl acetate in n-hexane IR γ$_{max}$ (thin film) : 2955, 2910, 2879, 1736, 1672, 1599, 1580, 1460, 1412, 1366, 1306, 1237, 1205, 1165, (broad), 1003, 974, 862, 837, 809, 736 cm$^{-1}$. Mass spectrum FAB(3-NOBA/Na matrix) observed mass MNa$^+$ 2016±1, calculated for C$_{107}$H$_{201}$NO$_{15}$Si$_9$Na$^+$, 2015.3.

DESCRIPTION 18

N-Trifluoroacetyl-16-(3-butenylcarbonyl)-16-decarboxy-3,5,8,9,11,15,35,2′,4′-nona-O-triethylsilyl-13,14-anhydroamphotericin B and 16-(3-butenylcarbonyl)-16-decarboxy-3,5,8,9,11,15,35,2′,4′-nona-O-triethylsilyl-13,14-anhydroamphotericin B

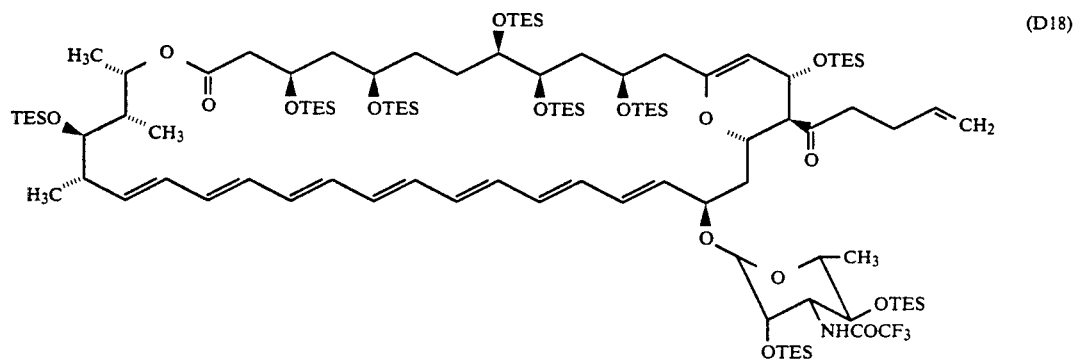

(D18)

and

-continued

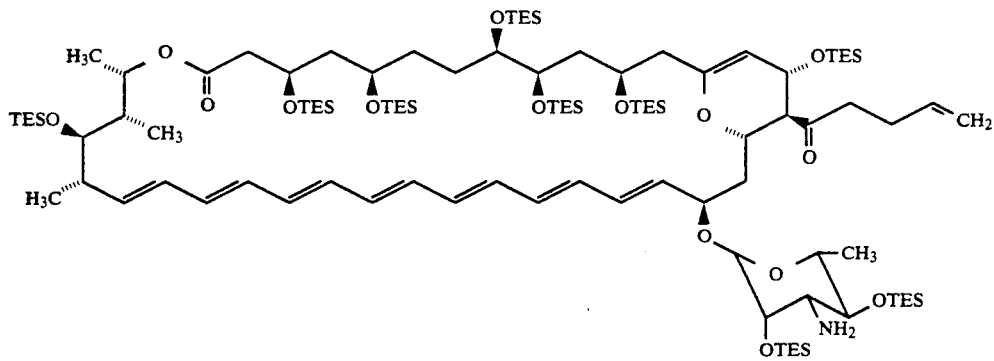

The pyridylthioester of Description 15 (344 mg, 0.162 mmol) was stirred at 0° C. in dry tetrahydrofuran (10 ml) under nitrogen and treated with vinylmagnesium bromide (2.43 ml of 1 M solution in tetrahydrofuran, 2.43 mmol). After stirring at 0° C. for 0.5 hours, saturated ammonium chloride solution was added and the product was extracted into diethyl ether. The combined organic extracts were dried over anhydrous magnesium sulphate, filtered and the filtrate evaporated.

Purification by column chromatography on silica gel eluting with n-hexane/ethyl acetate mixtures gave two major products.

The least polar N-trifluoroacetyl derivative has: Rf: 0.82 (silica, 10% ethyl acetate in n-hexane) δH 400 MHz ((CD$_3$)$_2$CO) includes 7.34 (1H,d,J 8.9 Hz,), 5.8 (1H,m), 5.08 (1H,m), 4.98 (1H,m), 4.64 (2H,s) 2.94 (1H, dd, J 10.5 and 8.9 Hz) ppm. IR γmax (thin film): 3425 (weak), 2955, 2910, 2875, 1735, 1710, 1670, 1525, 1460, 1410, 1375, 1240, 1165, 1075, 1005, 740, 725 cm$^{-1}$. Mass spectrum FAB (3-NOBA/Na) observed mass MNa$^+$ 2089, calculated for C$_{107}$H$_{202}$NO$_{16}$Si$_9$F$_3$Na$^+$, 2089.

The more polar amino derivative has: Rf: 0.36 (silica, 10% ethyl acetate in n-hexane) δH 400 MHz ((CD$_3$)$_2$CO) includes 5.87 (1H,m), 5.08 (1H,dd,J 17.1 and 1.6 Hz), 4.98 (1H,d,J 10.2 Hz), 4.63 (1H,s), 2.94 (1H,dd,J 10.7 and 8.5 Hz) ppm. IR γmax (thin film): 2950, 2905, 2875, 1735, 1710, 1670, 1640, 1460, 1410, 1375, 1240, 1190, 1165, 1090, 1005, 865, 740 cm$^{-1}$. Mass spectrum FAB (3-NOBA/Na) Observed mass MNa$^+$ 1993, calculated for C$_{105}$H$_{203}$NO$_{15}$Si$_9$Na$^+$, 1993.

DESCRIPTION 19

N-Trifluoroacetyl-16-decarboxy-16-(2-pyrrolylcarbonyl)-3,5,8,9,11,15,35,2',4'-nona-O-triethylsilyl-13,14-anhydroamphotericin B (D19)

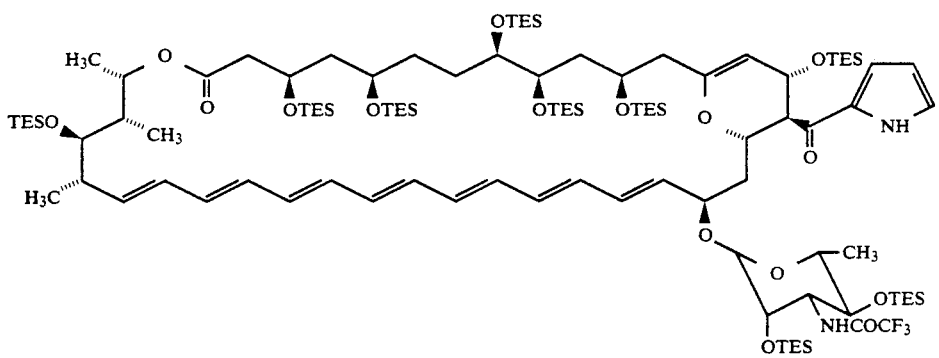

A solution of pyrrolylmagnesium bromide was prepared by treating pyrrole (354 mg, 0.366 ml, 5.30 mmol) in dry tetrahydrofuran (5 ml) with ethylmagnesium bromide (1.26 ml of 3M solution in diethyl ether, 3.77 mmol) at 0° C. under nitrogen. After stirring for 5 minutes at 0° C. and 5 minutes at room temperature, this Grignard solution was added via canula to an ice-cooled solution of the pyridylthio ester of Description 15 (402 mg, 0.189 mmol) in dry tetrahydrofuran (5 ml). The mixture was stirred for 20 minutes at 0° C. and then quenched with saturated ammonium chloride solution. The product was extracted into diethyl ether and the combined extracts were dried over anhydrous magnesium sulphate, filtered and the filtrate evaporated in vacuo. Purification by flash chromatography on silica gel, eluting with ethyl acetate/n-hexane mixtures gave the title compound (D19) as a yellow glass.

δH 400 MHz ((DC$_3$)$_2$CO): includes 11.09 (1H,s), 7.46 (1H,d,J 9.2 Hz), 7.24 (1H,m), 7.08 (1H,m), 4.68 (1H,s), 3.45 (1H,dd,J 11.0 and 8.6 Hz) ppm.

IR γmax (thin film): 3415, 3370, 2950, 2905, 2875, 1730, 1670, 1620. 1525, 1455, 1410, 1375, 1235, 1165, 1070, 1005, 870, 835, 760 cm$^{-1}$.

Mass spectrum: FAB (3-NOBA/Na) observed mass MNa$^+$ 2100.4, calculated for C$_{107}$H$_{199}$N$_2$O$_{16}$Si$_9$F$_3$Na$^+$, 2100.3.

EXAMPLE 1

N-Acetyl-16-acetyl-16-decarboxyamphotericin B (E1)

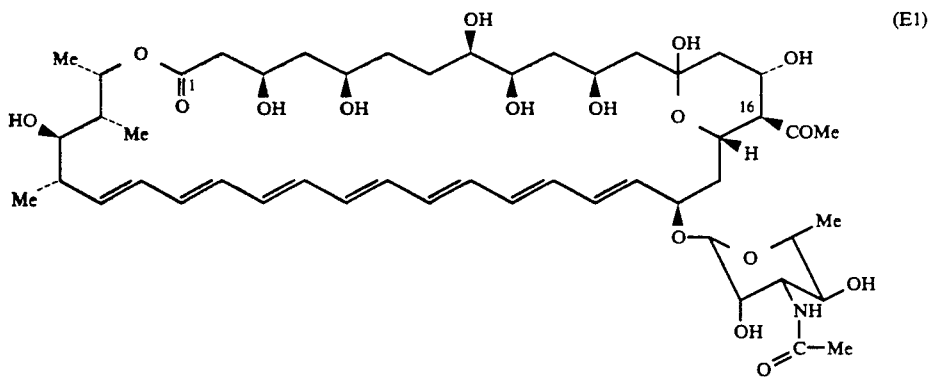

(E1)

The product mixture of Description 3 was stirred at room temperature in dry tetrahydrofuran (3 ml) in a plastic bottle and treated with a solution of Hydrogen fluoride-pyridine (7.00 ml of a solution of 1.93 g of hydrogen fluoridepyridine and 12.80 ml of pyridine in 50 ml of tetrahydrofuran). After stirring for 18 hours, the mixture was poured into diethyl ether (600 ml), and the precipated solid was collected by centrifugation Washing of the solid with diethyl ether and drying gave a yellow powder.

The powder was stirred in tetrahydrofuran (10 ml)/water (3 ml) with camphorsulphonic acid (0.014 g). After 1.25 hrs another 0.012 g of camphorsulphonic acid were added and the mixture was stirred for a further 0.75 hrs. Triethylamine (0.025 ml) was added, the tetrahydrofuran was removed in vacuo and the solid product was centrifuged from the aqueous residue. Drying gave a solid which was triturated with ethyl acetate to give a pale yellow powder. Purification by column chromatography on reverse phase silica eluting with tetrahydrofuran/water mixtures gave N-acetyl-16-acetyl-16-decarboxy amphotericin B.

IR $\gamma$max (KBr disc) : 3400 (broad), 2925,1720,1700,1658, 1375,1310,1180,1108,1065,1010,850 cm$^{-1}$.

$\delta$H (270 MHz),(d-6 DMSO): 7.63(1H,d,J 8.3 Hz), 6.55–6.05 (12H, series of m), 5.95(1H,dd,J 15 and 9 Hz), 5.94(1H,s, exchanges with D20), 5.43(1H,dd,J 13.5 and 9.9 Hz), 5.39(1H,s, exchanges with D$_2$0), 5.22(1H,m), 4.90(1H,d,J 6 Hz, exchanges With D$_2$0), 4.85–4.55(6H, multiplet, exchanges with D$_2$0), 4.45(1H,d,J 6 Hz, exchanges with D$_2$0), 4.32(1H,s), 4.35–4.17(3H,m), 4.09–3.88(2H,m), 3.70–3.35(4H,m), 3.20–2.95(4H,m), 2.50–2.05(5H, series of m), 2.15(3H,s), 1.95–1.0(14H, series of m), 1.85(3H,s), 1.14(3H,d,J 5.2 Hz), 1.11(3H,d,J 6.6 Hz), 1.03(3H,d,J 6.3 Hz), 0.91(3H,d, 6.9 Hz)ppm.

Mass spectrum FAB (3-NOBA/Na Matrix) Observed mass MNa+ 986, calculated for C$_{50}$H$_{77}$NO$_{17}$ Na+, 986.5.

HPLC : Reverse phase ODS 5 $\mu$ 250$\times$4.6mm column; eluant 78% methanol - 22% pH 3 phosphate buffer - 1 ml/min; detection wavelength 350nm; Retention time 8.0 minutes.

EXAMPLE 2

16-Acetyl-16-decarboxyamphotericin B (E2)

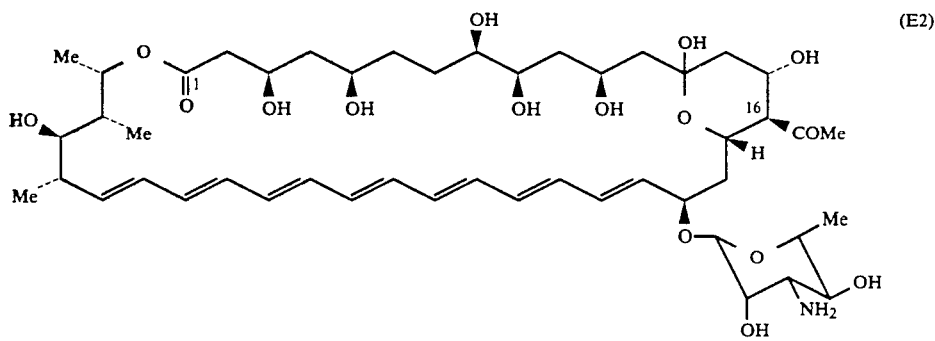

(E2)

The product of Description 16 (154 mg, 0.08 mmol) and hydrogen fluoride-pyridine solution (4.6 ml of a solution of 2.36 g of hydrogen fluoride-pyridine and 14 ml of pyridine made up to 63 ml in tetrahydrofuran) were stirred overnight at room temperature in a plastic bottle. The mixture was poured into diethyl ether/n-hexane (600 ml, 1:1) and the precipitated solid was collected by centrifugation, washed with diethyl ether, dissolved in methanol, filtered and concentrated to give a yellow powder.

The yellow powder was stirred at room temperature in tetrahydrofuran (3 ml)/water (1 ml) containing d-10-camphorsulphonic acid (8.0 mg) After stirring for 3.5 hours, triethylamine (0.01 ml) was added and the mixture was concentrated on the rotary evaporator. The crude product was triturated with diethyl ether/ethyl acetate to give the N-trifluoroacetyl derivative of the title compound as a yellow powder. This product was stirred at room temperature in tetrahydrofuran (5 ml), methanol (2.5 ml) and 0.880 ammonia solution (2.5 ml). After 4 hours another 3 ml of 0.880 ammonia solution was added and stirring was continued for a further 4 hours before storing the mixture in the freezer overnight. Another 2 ml of 0.880 ammonia solution was added and stirring continued for a further 6 hours at room temperature. The solvents were removed on the rotary evaporator and the residue was washed with diethyl ether and dried to give a brown solid. Purification by chromatography on silica gel eluting with the lower phase of chloroform/methanol/0.880 ammonia mixtures gave the title compound as a yellow powder.

Rf 0.32 (silica), 2:1:1 chloroform:methanol:0.880 ammonia (lower phase).

δH 400 MHz (d4-methanol/d5-pyridine 1:1) : 6.69–6.27(13H, series of m), 5.65(1H, m), 5.50(1H, dd, J 10.2, 14.8 Hz), 4.85(1H, m), 4.71(1H, s), 4.70–4.62(2H, m), 4.58(1H, ddd, J 4.6, 10.5, 10.8 Hz), 4.46(1H, tt, J 3.0, 9.7 Hz), 4.23(1H, d, J 3.0 Hz), (1H, m), 3.87(1H, m), 3.52(1H, t, J 9.3 Hz), 3.49–3.36(3H, m), 2.92(1H, dd, J 3.1, 9.4 Hz), 2.73(1H, t, J 10.5 Hz), 2.57(1H, m), 2.50(1H, dd, J 9.7, 16.8 Hz), 2.40(3H, s), 2.36(1H, dd, J 2.8, 16.8 Hz), 2.30(1H, J 4.6, 12.1 Hz), 2.20–2.08(2H, m), 2.06–1.97(2H, m), 1.90–1.48(10H, series of m), 1.44(3H, d, J 5.9 Hz), 1.36(3H, d, J 6.4 Hz), 1.25(3H, d, J 6.4 Hz), 1.17(3H, d, J 7.2 Hz)ppm.

IR γmax (KBr disc) 3380 (broad), 2920, 1700 (shoulder at 1721), 1445, 1366, 1307, 1268, 1180, 1104, 1063, 1009, 883, 845 cm$^{-1}$.

Mass spectrum FAB(Thioglycerol matrix) observed mass MH+ 922, calculated for $C_{48}H_{75}NO_{16}H^+$, 922.5.

EXAMPLE 3

16-Benzoyl-16-decarboxyamphotericin B (E3)

trated to give the 13,14-anhydro derivative of the title compound.

This product was stirred at room temperature in tetrahydrofuran (6 ml)/water (2 ml) containing d-10-camphorsulphonic acid (48 mg). Further batches of d-10-camphorsulphonic acid were added after 2 hrs (20 mg) and 3 hrs (32 mg) of the reaction. After stirring for a total of 5.5 hrs, triethylamine (0.08 ml) was added and the mixture was concentrated on a rotary evaporator. The crude product was dissolved in the minimum volume of tetrahydrofuran/dimethyl sulphoxide and added to diethyl ether (400 ml). The precipitated solid was collected by centrifugation and chromatographed on silica gel, eluting with 5:2:2 chloroform:methanol:0.880 ammonia solution (lower phase) to give the title compound as a yellow solid.

Rf : 0.32 (silica), 2:1:1 chloroform:methanol: 0.880 ammonia solution (lower phase). δH 400 MHz (d4-methanol/d5-pyridine 1:1) : 8.30(2H m), 7.64(1H, m), 7.56(2H, m), 6.69–6.24(13H, series of m), 5.66(1H, m), 5.50(1H, dd, J 14.9, 10.2 Hz), 5.01(1H, t, J 4.7, 9.5 Hz), 4.87(1H, ddd, J 4.7, 10.1, 11.1 Hz), 4.70 (1H, m), 4 61(1H, m), 4.47(1H, m), 4.46(1H, s), 4.31(1H, d, J 3.1Hz), 3.98(1H, m), 3.89(1H, m), 3.80(1H, t, J 10.1 Hz), 3.55(1H, J 9.5 Hz), 3.47(1H, m), 3.38(1H, dd, J 2, 9.5 Hz), 3.25(1H, dq, J 6.1, 9.1 Hz), 2.97(1H, dd, J 3.0, 9.8 Hz), 2.58(1H, m), 2.50(1H, dd of ABX system J 9.6, 16 8 Hz), 2.40(1H, dd, J 4.7, 11.7 Hz), 2.36(1H, dd of ABX system, J 2.8, 16.8 Hz),2.22–1.97(4H, series of m),

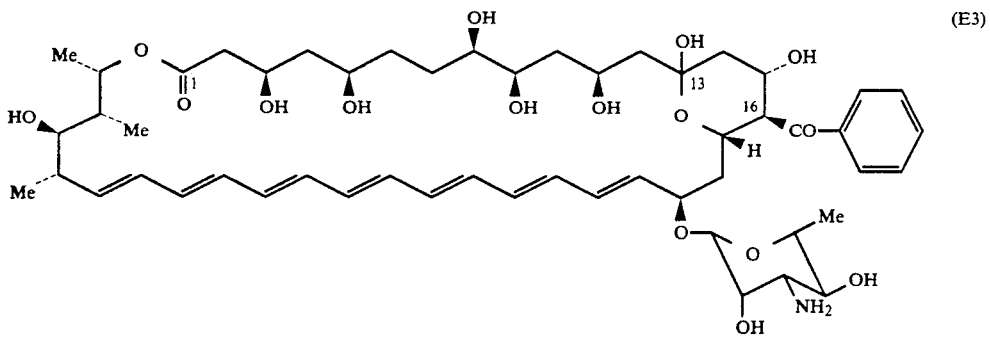

(E3)

The free amino product of Description 17 (248 mg, 18 0.12 mmol) and hydrogen fluoride-pyridine solution (7.60 ml of a solution of 2.36 g of hydrogen fluoridepyridine and 14 ml of pyridine made up to 63 ml in tetrahydrofuran) were stirred for 18 hours at room temperature in a plastic bottle. The mixture was poured into diethylether/n-hexane (1 L, 1:1) and the solid product was collected by centrifugation, washed with diethyl ether, dissolved in methanol, filtered and concen- 1.92(1H, dd, J 11.0, 13.9 Hz), 1.86–1.47(9H, series of m), 1.37(3H, d, J 6.1 Hz), 1.36(3H, d, J 6.4 Hz), 1.25(3H, d, J 6.4 Hz), 1.17(3H, d, J 7.%Hz)ppm.

Mass spectrum : FAB(thioglycerol matrix) observed mass MH+ 984, calculated for $C_{53}H_{77}NO_{16}H^+$, 984.5

EXAMPLE 4

16-(3-Butenylcarbonyl)-16-decarboxyamphotericin B (E4)

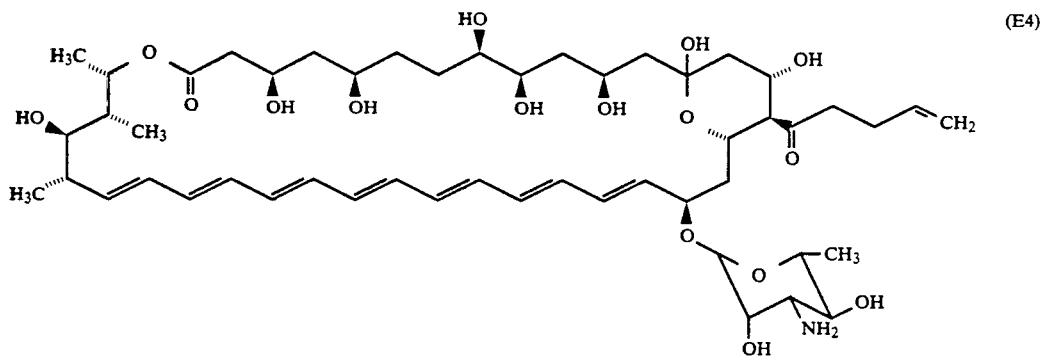

The free amino product of Description 18 (109 mg, 0.055 mmol) and hydrogen fluoride-pyridine (2.2 ml of a solution of 11.4 g of hydrogen fluoride-pyridine and 80 ml of pyridine made up to 200 ml with tetrahydrofuran) were stirred for 18hrs at room temperature under nitrogen in a plastic bottle. The mixture was poured into diethyl ether/n-hexane (200 ml,1:1) and the precipitated product was collected by filtration, washed with diethyl ether, dissolved in methanol and the solution concentrated in vacuo. Purification by flash chromatography on silica gel, eluting with 5:2:2 chloroform: methanol 0.880 ammonia solution (lower phase) gave a yellow powder.

This product was stirred in tetrahydrofuran (3 ml)/water (1 ml) at room temperature and treated with pyridinium p-toluenesulphonate (30 mg). After 2hrs more pyridinium p-toluenesulphonate (23 mg) was added and the mixture was stirred at room temperature for 6hrs, stored in the freezer overnight and then stirred at room temperature for a further 8 hrs. A few drops of triethylamine were added and the tetrahydrofuran was removed on the rotary evaporator. The residue was added to water (200 ml) and the precipitated product was collected by filtration, washed with water and dried in vacuo. Purification by flash chromatography on silica gel, eluting with 5:2:2 chloroform:methanol: 0.880 ammonia solution (lower phase) gave the title compound (E4) as a yellow powder.

δH 400 MHz (d4-methanol/d5-pyridine 1:1): includes 5.93 (1H,m), 5.12 (1H,m), 5.02 (1H,m) and 2.75 (1H,t,J 10.4 Hz) ppm.

Mass spectrum: FAB (Thiodiethanol/Na) Observed mass MNa+ 984, calculated for $C_{51}H_{79}NO_{16}Na^+$, 984.5.

EXAMPLE 5

16-Decarboxy-16-(2-pyrrolylcarbonyl)amphotericin B (E5)

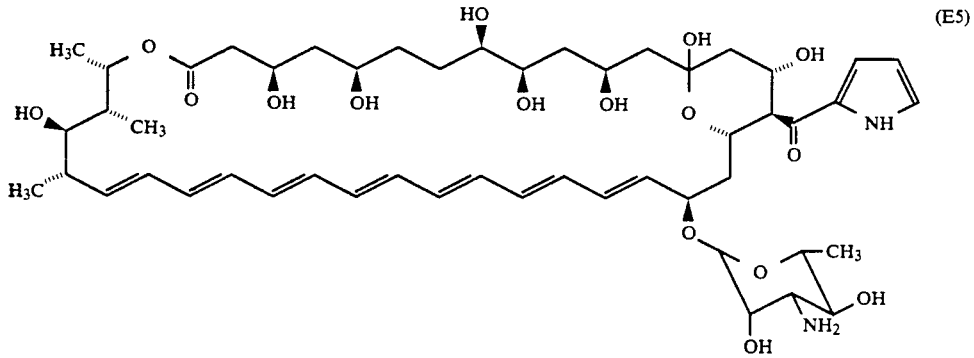

The product of Description 19 (320 mg, 0.154 mmol) and hydrogen fluoride-pyridine (5.7 ml of a solution of 15.5 g of hydrogen fluoride-pyridine and 92 ml of pyridine made up to 250 ml with tetrahydrofuran) were stirred in dry tetrahydrofuran (5 ml) at room temperature under nitrogen in a plastic bottle. After 18hrs, the mixture was poured into diethyl ether/n-hexane (400 ml, 1:1) and the precipitated product was collected by filtration and washed with diethyl ether. The product was dissolved in tetrahydrofuran, filtered through a short column of silica gel and the eluent concentrated in vacuo to give a yellow powder. This product was stirred at room temperature in tetrahydrofuran (4 ml)/water (2 ml) with camphorsulphonic acid (15.6 mg). After 0.25 hours more camphorsulphonic acid (19.0 mg) was added and stirring was continued for a further 3.25 hours. Triethylamine (23 mg, 0.031 ml) was added and the tetrahydrofuran was removed on the rotary evaporator. The aqueous residue was added to water (400 ml) and the precipitated product was collected by filtration, washed with water and dried to give a yellow/brown powder.

This product was stirred at room temperature in tetrahydrofuran (5 ml), methanol (5 ml) and 0.880 ammonia solution (5 ml). After 3 hours the mixture was stored in the freezer overnight and then stirred at room temperature for a further 8 hours. The solvents were removed on the rotary evaporator and the crude product was purified by a combination of column chromatography and preparative TLC on silica eluting with the lower phase of chloroform/methanol/0.880 ammonia mixtures to give the title compound (E5) as a yellow/brown powder.

δH 400 MHz (d$_4$-methanol/d$_5$-pyridine 1:1); includes 7.36 (1H,m, partially masked by solvent), 7.27 (1H,dd,J 2.4 and 1.3 Hz), 6.69–6.24 (14H, series of m), 3.38 (1H,t,J 10.3 Hz) ppm.

IR γmax (KBr disc): 3350 (broad), 2910, 1705, 1610, 1395, 1320, 1175, 1100, 1045, 1005, 880, 845, 810, 755 cm$^{-1}$.

Mass spectrum: FAB (Thiodiethanol/Na) Observed mass MNa$^+$ 995, calculated for C$_{51}$H$_{76}$N$_2$O$_{16}$Na$^+$, 995.5 UV (methanol) λmax 406, 382, 363, 345 nm.

MIC DATA

METHOD

The Minimum Inhibitory Concentration (MIC) was determined by diluting the test compound in a broth medium in a microtitre tray. The organisms, which had been grown previously in a broth medium, were diluted and added to the wells to provide a final inoculum of approximately 10$^5$ colony-forming units per well. The trays were incubated at 37° C. and the turbidity of each well noted at intervals. The MIC was taken as the lowest concentration (in μg/ml) which prevented significant growth.

RESULTS

| | | Minimum Inhibitory Concentration (μg/ml) (determined after 2 and 3 days incubation) | | |
|---|---|---|---|---|
| | | EXAMPLE 2 | | EXAMPLE 3 |
| ORGANISM* | DAY | YNB | SAB | YNB | SAB |
| Candida albicans | 2 | 2 | 0.5 | 1 | 1 |
| 73/079 | 3 | 2 | 0.5 | 4 | 1 |
| Candida | 2 | 4 | 2 | 4 | 2 |
| parapsilosis | 3 | 4 | 4 | 8 | 4 |
| 937 A | | | | | |

*Inoculum 10$^5$ cells/ml
YNB: Yeast Nitrogen Base Broth
SAB: Sabouraud's Dextrose Broth.

We claim:

1. A compound of formula (I) or a pharmaceutically acceptable salt thereof:

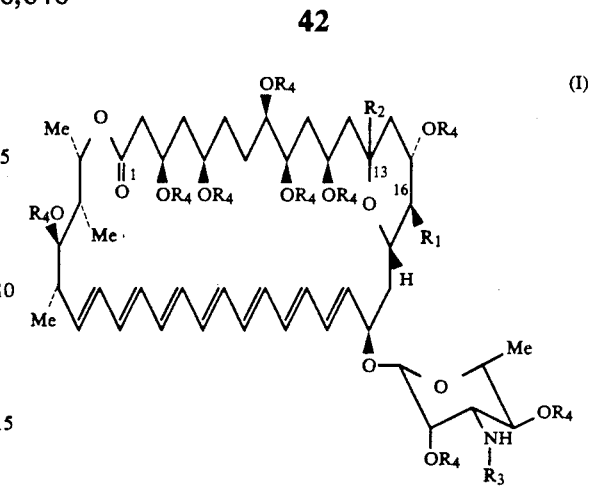

wherein R$_1$ is a group -X-Y where X is a carbonyl group and Y is hydrogen, C$_{1-8}$ alkyl, C$_{2-8}$ alkenyl, or optionally substituted phenyl, naphthyl, a 5- or 6-membered monocyclic or 9- or 10-membered bicyclic heteroaryl containing one or two hetero atoms selected from the group consisting of nitrogen, oxygen and sulphur, which in the case of there being more than one heteroatom may be the same or different; and in which the optional substituents are selected from the group consisting of OH, C$_{1-6}$ alkyl, C$_{1-6}$ alkoxy, halogen and amino optionally substituted by C$_{1-6}$ alkyl; R$_2$ is hydroxy or C$_{1-8}$ alkoxy; R$_3$ is hydrogen or an amine protection group selected from the group consisting of acetyl, trifluoroacetyl, 9-fluroenylmethoxycarbonyl, trichloroethoxycarbonyl, 2-methylsulphonylethoxycarbonyl and 2-trimethylsilylethoxycarbonyl and each R$_4$ is hydrogen.

2. A compound according to claim 1, wherein R$_1$ is formyl, acetyl, pent-4-enoyl, benzoyl or 2-pyrrolylcarbonyl.

3. A compound according to claim 1 wherein R$_2$ is hydroxy or methoxy.

4. A compound according to claim 1 wherein R$_1$ is selected from the group consisting of formyl, acetyl, pent-4-enoyl, benzoyl and 2-pyrrolylcarbonyl; R$_2$ is hydroxy or methoxy; R$_3$ is hydrogen or selected from the group consisting of acetyl, trifluoroacetyl and 9-fluorenylmethoxycarbonyl; and each R$_4$ is hydrogen.

5. A compound selected from the group consisting of:
N-acetyl-16-acetyl-16-decarboxyamphotericin B;
16-acetyl-16-decarboxyamphotericin B;
16-benzoyl-16-decarboxyamphotericin B;
16-(3-butenylcarbonyl)-16-decarboxyamphotericin B; and
16-decarboxy-16-(2-pyrrolylcarbonyl)-amphotericin B.

6. A pharmaceutical composition comprising an antifungally active amount of compound of formula (I) or a pharmaceutically acceptable salt thereof, as defined in claim 1, together with a pharmaceutically acceptable diluent or carrier.

7. A method of treatment of fungal infections in animals, which comprises administering an effective antifungal amount of a compound of formula (I) or a pharmaceutically acceptable salt thereof, as defined in claim 1, to an animal in need of such treatment.

* * * * *